(12) United States Patent
Pettersson et al.

(10) Patent No.: US 10,684,285 B2
(45) Date of Patent: Jun. 16, 2020

(54) DIAGNOSTICS OF GYNEACOLOGICAL DISEASES, ESPECIALLY EPITHELIAL OVARIAN CANCER

(71) Applicant: KAIVOGEN OY, Turku (FI)

(72) Inventors: Kim Pettersson, Turku (FI); Kamlesh Gidwani, Shahganj (IN)

(73) Assignee: KAIVOGEN OY, Turku (FI)

( * ) Notice: Subject to any disclaimer, the term of this patent is extended or adjusted under 35 U.S.C. 154(b) by 0 days.

(21) Appl. No.: 15/577,631

(22) PCT Filed: Jul. 4, 2016

(86) PCT No.: PCT/FI2016/050490
§ 371 (c)(1),
(2) Date: Nov. 28, 2017

(87) PCT Pub. No.: WO2017/005974
PCT Pub. Date: Jan. 12, 2017

(65) Prior Publication Data
US 2018/0156806 A1 Jun. 7, 2018

(30) Foreign Application Priority Data
Jul. 3, 2015 (FI) .................................... 20155531

(51) Int. Cl.
*G01N 33/53* (2006.01)
*G01N 33/574* (2006.01)
*G01N 33/543* (2006.01)
*G01N 33/566* (2006.01)

(52) U.S. Cl.
CPC . *G01N 33/57449* (2013.01); *G01N 33/54313* (2013.01); *G01N 33/566* (2013.01); *G01N 33/57442* (2013.01); *G01N 2800/364* (2013.01)

(58) Field of Classification Search
CPC ....... G01N 33/57449; G01N 33/54313; G01N 33/566; G01N 33/57442; G01N 2800/364; G01N 33/53
See application file for complete search history.

(56) References Cited

U.S. PATENT DOCUMENTS

2005/0245737 A1* 11/2005 Cummings ............... C07H 5/04
536/55.3
2012/0065089 A1* 3/2012 Kuno .................... G01N 21/648
506/9

FOREIGN PATENT DOCUMENTS

| CN | 103604920 A | 2/2014 |
|----|-------------|--------|
| EP | 2 463 300 A2 | 6/2012 |
| JP | 2012-154881 A | 8/2012 |
| KR | 10-2014-0011760 | 1/2014 |
| WO | WO 2008/007941 A1 | 1/2008 |
| WO | WO 2013/023994 A1 | 2/2013 |
| WO | WO 2014/120902 A1 | 8/2014 |

OTHER PUBLICATIONS

Chen (J. Proteome Research;2013 Mar. 1;12(3):1408-18 and Supplemental data).*
Suzuki et al. (J. Immunol 1996;156:128-135).*
Harma et. al. (Clin. Chem;2001, 47:3,561-2001).*
Akita et al., "Different Levels of Sialyl-Tn Antigen Expressed on MUC16 in Patients with Endometriosis and Ovarian Cancer." Int. J. Gynecol. Cancer (2012), vol. 22, pp. 531-538.
Chen et al., "Microarray Glycoprofiling of CA125 Improves Differential Diagnosis of Ovarian Cancer." J. Proteome Res. (2013), vol. 12, pp. 1408-1418
Hallamaa et al., "Serum HE4 concentration is not dependent on menstrual cycle or hormonal treatment among endometriosis patients and healthy premenopausal women." Gynecologic Oncology (2012), vol. 125, pp. 667-672.
International Search Report dated Oct. 4, 2016, in PCT International Application No. PCT/FI2016/050490.
Jankovic, M. M. and B. S. Milutinovic, "Glycoforms of CA125 antigen as possible cancer marker," Cancer Biomarkers (2008), vol. 4, pp. 35-42.
Office Action dated Mar. 3, 2016, in Finnish Patent Application No. 20155531.
Ricardo et al., "Detection of glyco-mucin profiles improves specificity of MUC16 and MUC1 biomarkers in ovarian serous tumours,"Molecular Oncology (Oct. 22, 2014), vol. 9, No. 2, pp. 503-512
Ricardo et al., Abstract 696 "Glycoprofiling of serous ovarian tumours is a promising strategy for developing new diagnostic tools," EACR-23 Poster Sessions, European Journal of Cancer, vol. 50, Suppl. 5, p. S167 (2014).
Search Report dated Mar. 3, 2016, in Finnish Patent Application No. 20155531.
Soukka et al., "Utilization of Kinetically Enhanced Monovalent Binding Affinity by Immunoassays Based on Multivalent Nanoparticle-Antibody Bioconjugates." Anal. Chem. (May 15, 2001), vol. 73, No. 10, pp. 2254-2260.
van Kooyk et al., "Novel insights into the immunomodulatory role of the dendric cell and macrophage-expressed C-type lectin MGL," Immunobiology (2014), vol. 220, pp. 185-192.
Japanese Office Action, dated Dec. 4, 2018, for Japanese Application No. 2017-567297, with an English translation.
Jégouzo et al., "Organization of the extracellular portion of the macrophage galactose receptor: A trimetric cluster of simple binding sites for N-acetylgalactosamine", Glycobiology, vol. 23, No. 7, 2013, pp. 853-864.

* cited by examiner

*Primary Examiner* — Julie Wu
*Assistant Examiner* — Carmencita M Belei
(74) *Attorney, Agent, or Firm* — Birch, Stewart, Kolasch & Birch, LLP

(57) ABSTRACT

The present disclosure relates to methods and a kit for diagnosing, prognosing and/or monitoring a gynaecological disease, especially epithelial ovarian cancer, on the basis of altered glycosylation pattern of CA125. More specifically, said altered glycosylation pattern relates to that recognizable by MGL.

20 Claims, 19 Drawing Sheets

DIAGNOSTICS OF GYNAECOLOGICAL DISEASES, ESPECIALLY EPITHELIAL OVARIAN CANCER

FIELD OF THE INVENTION

The present disclosure relates to the non-invasive diagnostics of gynaecological diseases, especially epithelial ovarian cancer (EOC), on the basis of altered glycosylation pattern of CA125, and provides various methods of diagnosing, prognosing, or monitoring gynaecological diseases, including EOC.

BACKGROUND OF THE INVENTION

Early cancer detection with sensitive and accurate biomarkers is a key to successful cancer treatment. Such biomarkers are especially important for cancers, which remain asymptomatic until disseminated stage, when curative response can rarely be achieved. Epithelial ovarian cancer (EOC) is a major health care problem as early detection with sufficient sensitivity and specificity is lacking. The 5-year survival rate for women diagnosed at the early stage is 90% whereas it is 20% if detected during late stage.

Human cancer antigen 125 (CA125), also known as mucin 16 or MUC16, is a complex transmembrane glycoprotein and the most widely used biomarker for EOC. It plays an important role not only in the diagnosis of primary epithelial ovarian cancer but also in the disease monitoring of postoperative women. The existing CA125 assays are double-determinant immunoassays based on detection of two different CA125 protein epitopes by two different monoclonal antibodies.

However, CA125 lacks sensitivity and cancer-specificity, especially at the early stages of EOC, owing to its elevated expression also in benign gynaecological conditions such as benign ovarian neoplasms and endometriosis, as well as in liver disease, and even during the normal ovulatory cycle. Therefore, CA125 is not recommended for screening of EOC.

During cancer progression, glycosylation patterns of many proteins change. Thus, detecting cancer related glycosylation patterns could offer novel diagnostic approaches for achieving improved specificity in tumor detection. Indeed, altered glycan composition has been reported in ovarian carcinoma compared to normal ovarian tissue, and further, altered glycan structures have been reported in serum CA125 of patients with EOC.

Chen et al. (J. Proteome Res., 2013, 12, 1408-1418) have reported that aberrant O-glycoforms of CA125 are present in serum from primary EOC patients and can be detected with a sandwich immunoassay using an O-glycan specific monoclonal antibody and VVL (*Vicia Villosa* lectin).

Although glycoprofiling of known tumor markers, such as CA125, and the use of a panel of different tumor markers seem to be promising for increasing the sensitivity and specificity of ovarian cancer detection through the elimination of many false positive results, there is still need for more specific markers which enable sufficient, easy-to-use discrimination between benign diseases and early, curable epithelial ovarian cancers.

BRIEF DESCRIPTION OF THE INVENTION

In one aspect, the present disclosure provides a method of determining a gynaecological disease state in a subject. Said method comprises the steps of:

assaying a sample obtained from said subject for the level of CA125 which binds to macrophage galactose-type lectin (CA125MGL), comparing the detected level of CA125MGL in said sample with that of a control sample or a predetermined threshold value, and determining the gynaecological disease state in said subject on the basis of said comparison.

In some embodiments, increased level of $CA125^{MGL}$ indicates that said subject has or is at risk of having epithelial ovarian cancer (EOC), while non-increased level of $CA125^{MGL}$ indicates that said subject does not have or is not at risk of having EOC but may have or be at risk of having endometriosis or endometrial cancer, or may be apparently healthy also with respect to endometriosis or endometrial cancer.

In some further embodiments, the method may further comprise assaying a sample obtained from said subject for CA125 protein concentration, and comparing the detected CA125 protein concentration with that of a control sample or a predetermined threshold value. Increased CA125 protein concentration in combination with increased level of $CA125^{MGL}$ would further indicate that said subject has or is at risk of having EOC, while increased CA125 protein concentration in combination with non-increased level of $CA125^{MGL}$ would indicate that said subject has or is at risk of having endometriosis.

Alternatively or in addition, the method may further comprise assaying a sample obtained from said subject for the HE4 concentration, and comparing the detected HE4 concentration with that of a control sample or a predetermined threshold value. Increased HE4 concentration in combination with increased level of $CA125^{MGL}$ would further indicate that said subject has or is at risk of having EOC, while increased HE4 concentration in combination with non-increased level of $CA125^{MGL}$ would indicate that said subject has or is at risk of having endometrial cancer.

The present method may be used, for example, for differential diagnostics of a gynaecological disease selected from the group consisting of EOC, endometriosis, or endometrial cancer, or for diagnosing, prognosing, or monitoring a gynaecological disease selected from the group consisting of EOC, endometriosis, or endometrial cancer. In some embodiments said monitoring may encompass monitoring onset of said gynaecological disease, for monitoring any change in risk of having or developing said gynaecological disease, for monitoring response to treatment, for monitoring relapse of said gynaecological disease, or for monitoring recurrence of said gynaecological disease.

In some further embodiments, said assaying of the level of $CA125^{MGL}$ may be carried out by assaying the level of CA125 binding to said MGL-NP, which assaying may comprise capturing CA125 contained in the sample using a capturing agent, such as an anti-CA125 antibody or mesothelium, and measuring said captured CA125 for the level of binding to MGL-NP with the aid of a detectable signal. In other words, said sample is assayed for the amount of $CA125^{MGL}$ by using a CA125 binding agent and detectably labelled MGL-NP.

In some other embodiments, said assaying of the level of $CA125^{MGL}$ may be carried out by assaying the level of CA125 binding to said MGL-NP, which assaying may comprise subjecting said sample to MGL-NP in order to capture MGL-binding glycoform of CA125 contained in the sample, and measuring the amount of captured CA125 using a CA125 binding agent, such as an anti-CA125 antibody or mesothelium, with the aid of a detectable signal. In other words, said sample is assayed for the amount of $CA125^{MGL}$ by using MGL-NP and a detectably labelled CA125 binding agent.

In another aspect, the present disclosure provides a kit for use in any of the methods disclosed herein. Said kit comprises a CA125-binding agent, such as a monoclonal anti-CA125 antibody or mesothelium, and a MGL-NP. Either said CA125-binding agent or said MGL-NP comprises a detectable label. In some embodiments, either said CA125-binding agent or said MGL-NP is bound to a solid surface, such as a microtiter plate.

In a further aspect, the present disclosure provides a MGL-NP as set forth below. Said MGL-NP may be used, for example, in diagnosing, prognosing and/or monitoring a gynaecological disease state in a subject. Preferably, said gynaecological disease is selected from the group consisting of EOC, endometriosis and endometrial cancer.

Other objectives, aspects, embodiments, details and advantages of the present invention will become apparent from the following figures, detailed description, examples, and dependent claims.

BRIEF DESCRIPTION OF THE DRAWINGS

In the following the invention will be described in greater detail by means of preferred embodiments with reference to the attached drawings, in which.

Figure 12A:
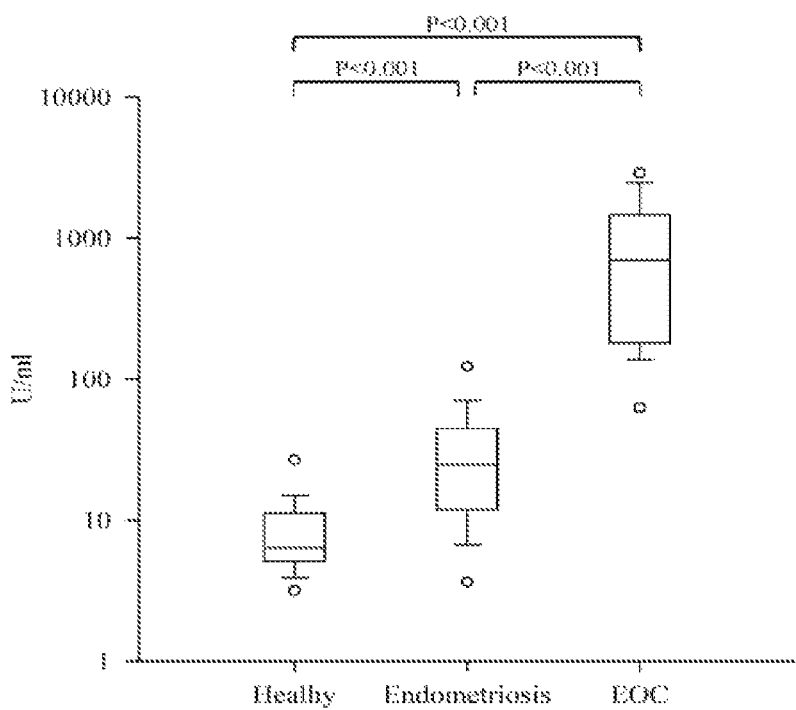
Figure 12B:
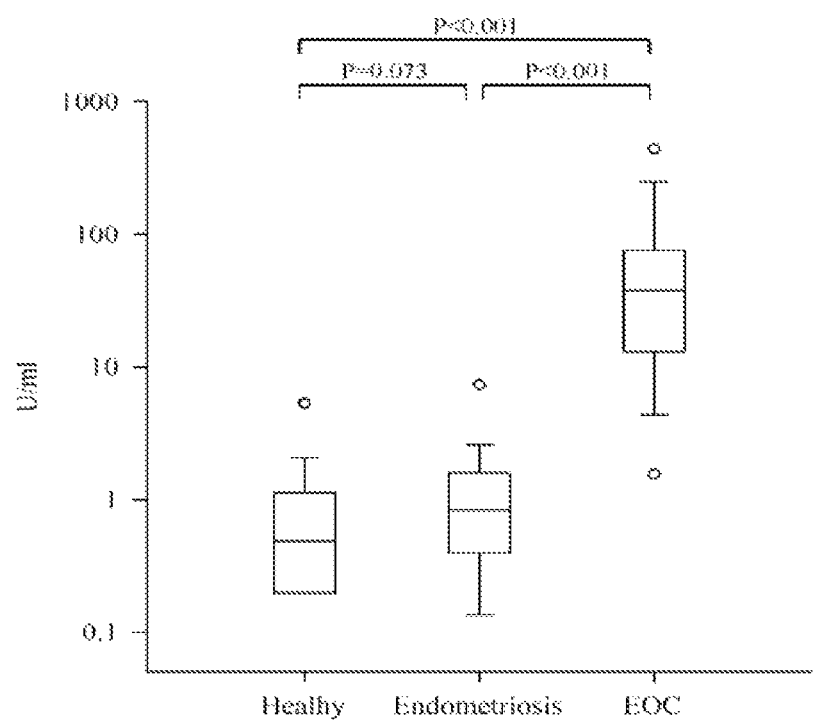
Figure 12C:
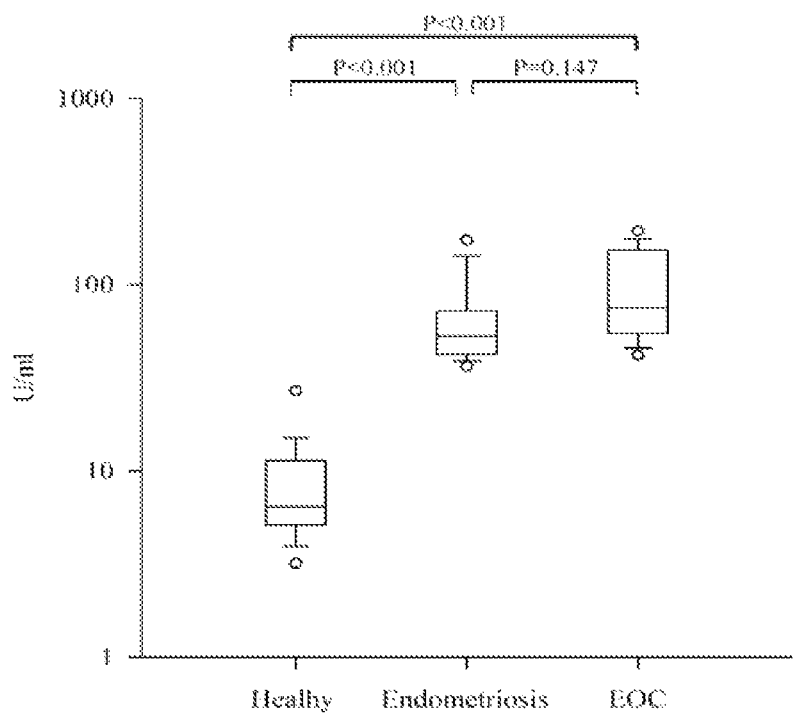
Figure 12D:
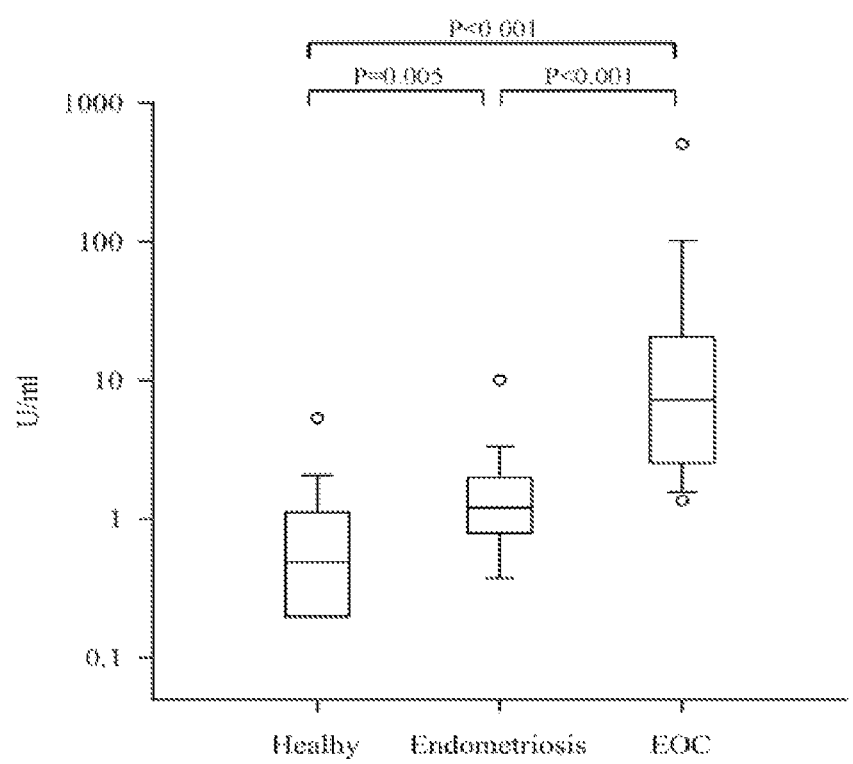

FIGS. 12A to 12D show Box Plot presentations which demonstrate discrimination of EOC from benign endometriosis and healthy controls using conventional CA125 immunoassay (FIGS. 12A and 12C) and CA125$^{MGL}$-assay (FIGS. 12B and 12D). FIG. 12 shows that CA125 in preoperative high-grade serous EOC (n=21) and endometriosis (n=121) were significantly higher than in healthy controls (n=51) with conventional CA125 immunoassay (p<0.001). FIG. 12B shows that no significant difference between endometriosis and healthy controls was observed in CA125$^{MGL}$ levels while preoperative EOC levels were significantly higher (p<0.001). FIG. 12C shows that EOC (n=38) and endometriosis (n=44) samples with marginally elevated CA125 concentrations (35-200 U/ml), which are clinically the most challenging for diagnostics, did not differ with CA125 immunoassay, while FIG. 12D shows that CA125$^{MGL}$ levels remained significantly different.

Figure 13A:
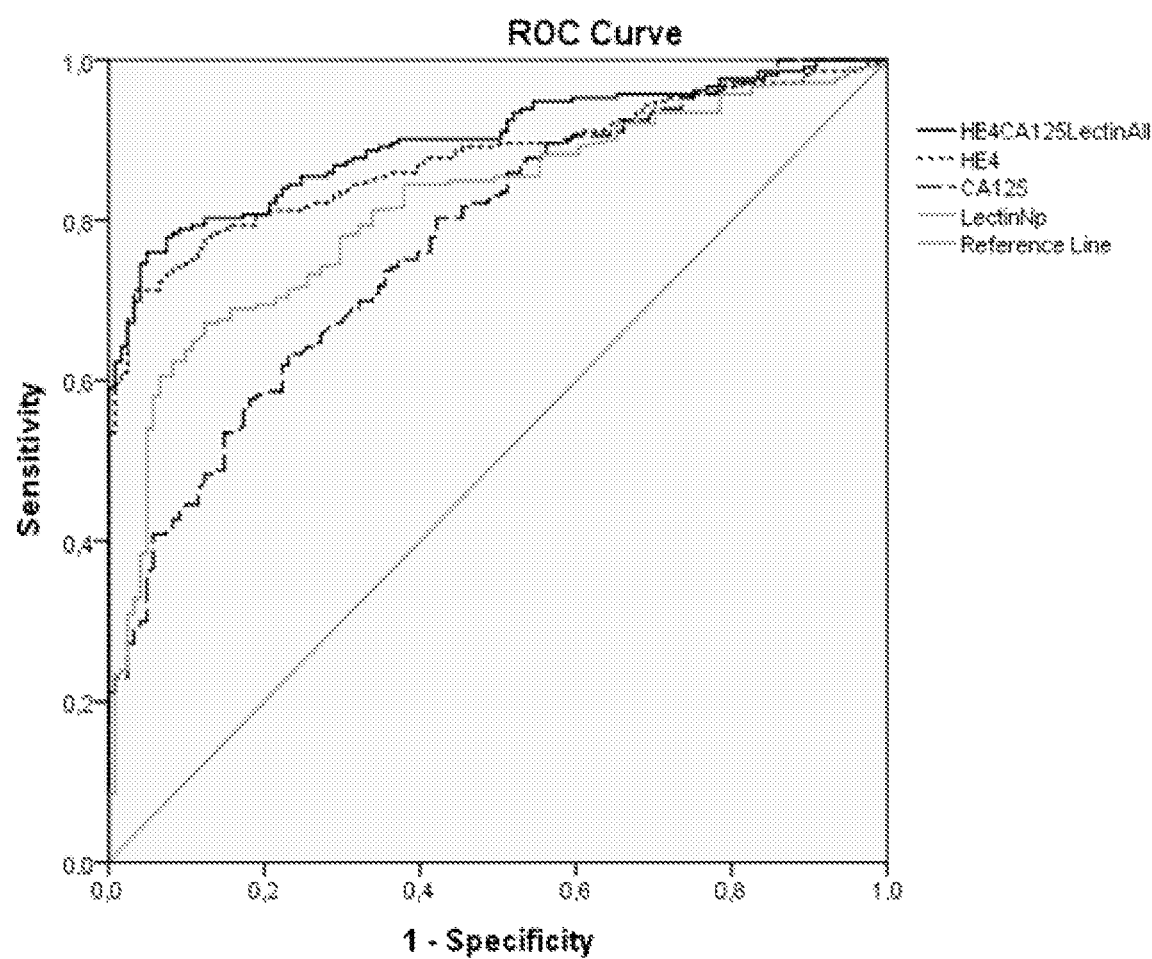

FIG. 13A shows ROC curves for HE4, CA125, and CA125$^{MGL}$ either alone or in combination in a cohort of all sequential EOC cases (n=213) vs. endometriosis cases (n=133). The highest AUC value was obtained with a combination of all three markers.

Figure 13B:
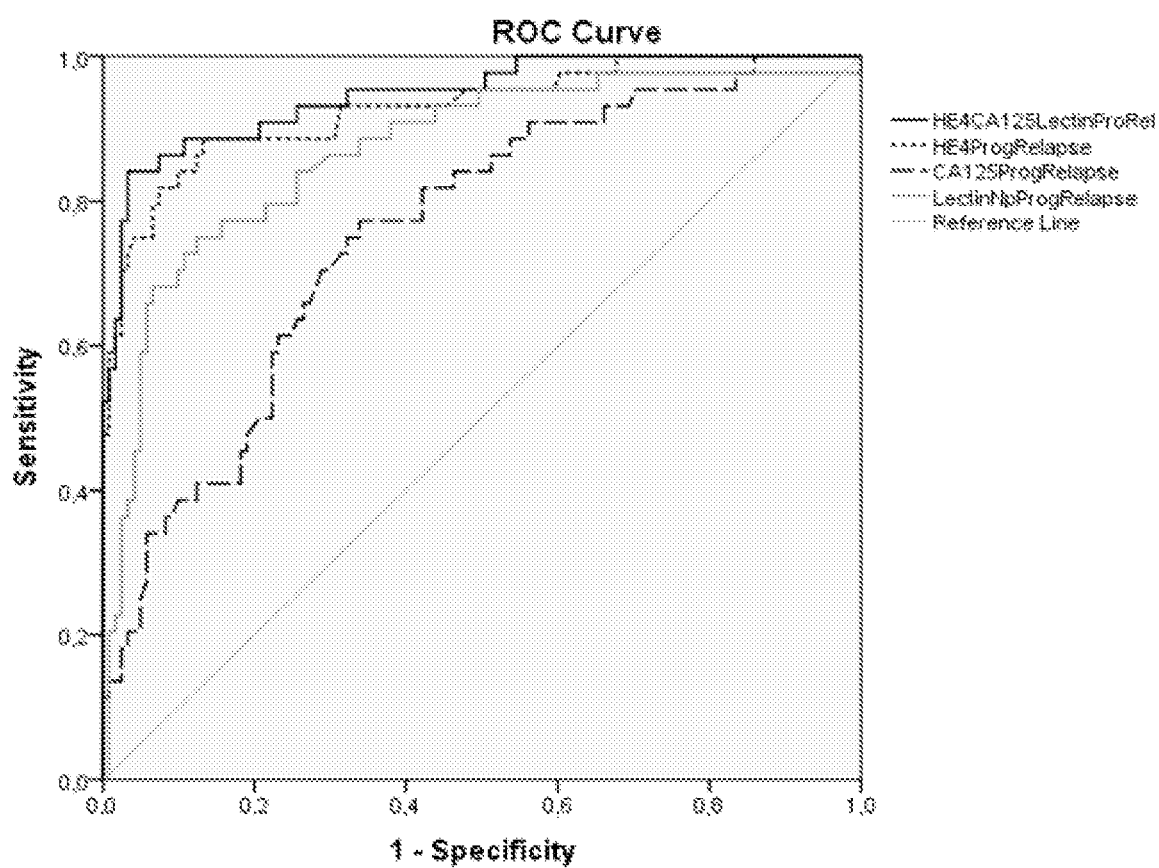

FIG. 13B shows ROC curves for HE4, CA125, and CA125$^{MGL}$ either alone or in combination in a cohort of progression/relapse cases of EOC (n=43) vs. endometriosis (n=133). The highest AUC value was obtained with a combination of all three markers.

Figure 13C:
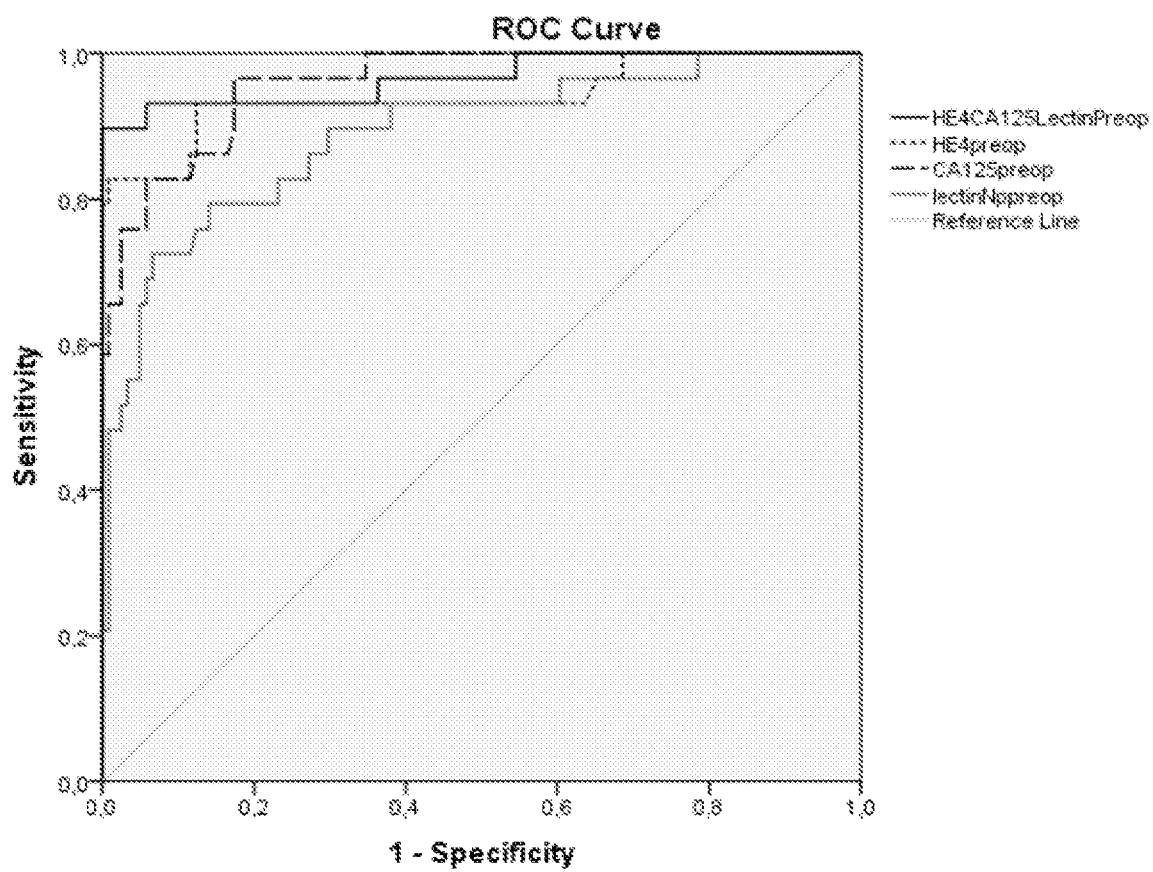

FIG. 13C shows ROC curves for HE4, CA125, and CA125$^{MGL}$ either alone or in combination in a cohort of pre-treatment EOC cases (n=29) vs. endometriosis (n=133). All markers show high AUC values but the highest AUC value was obtained with a combination of all three markers.

Figure 14:
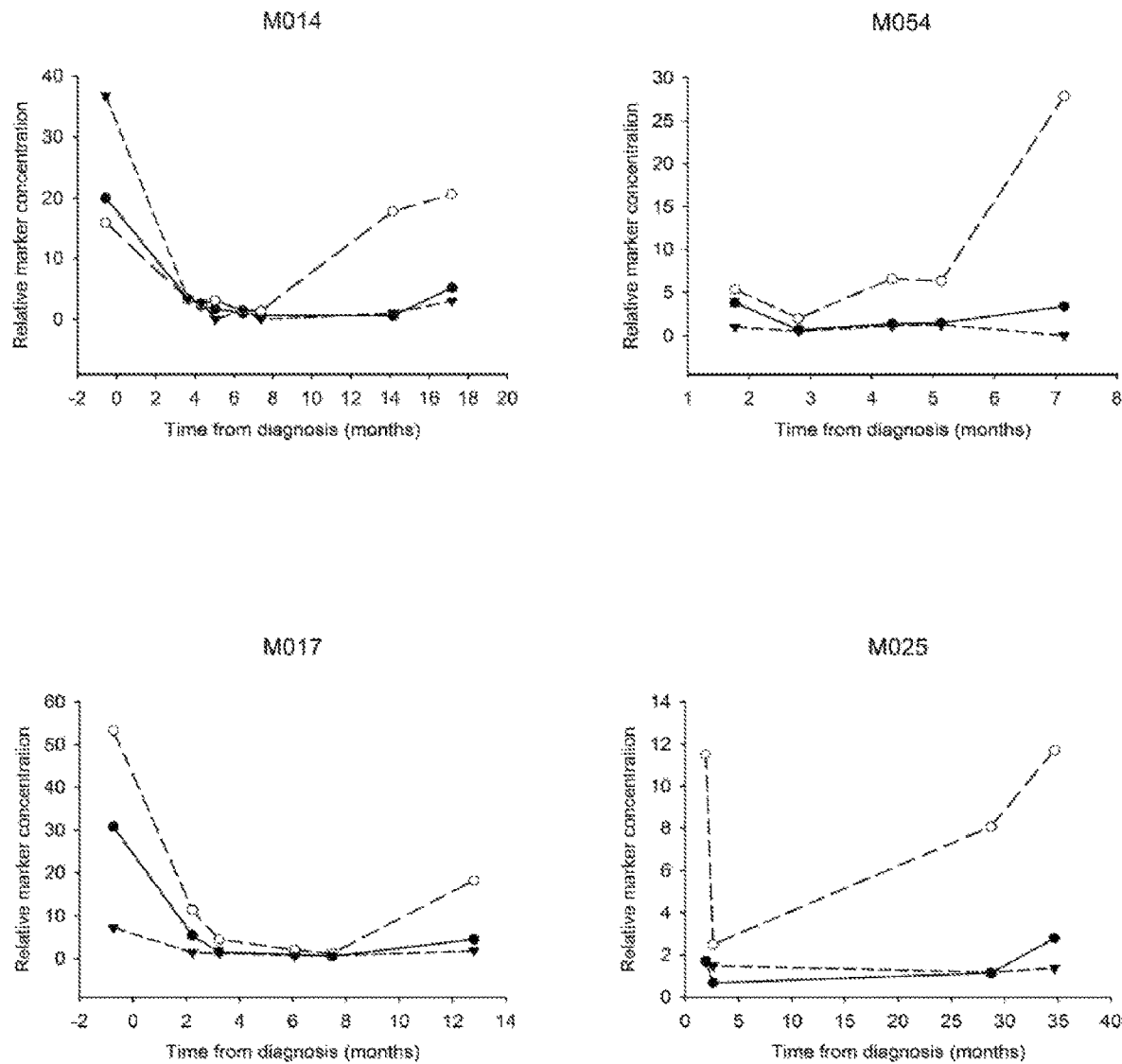
Figure 14:
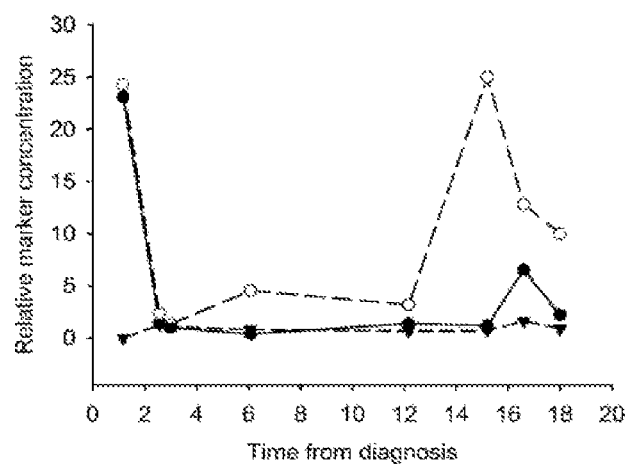
Figure 14:
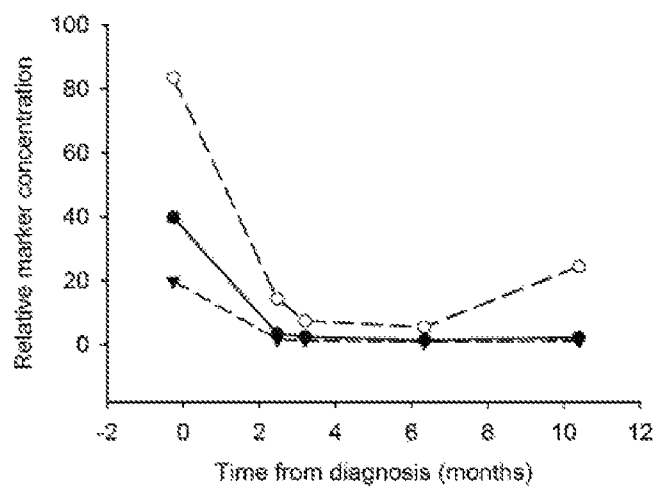
Figure 14:
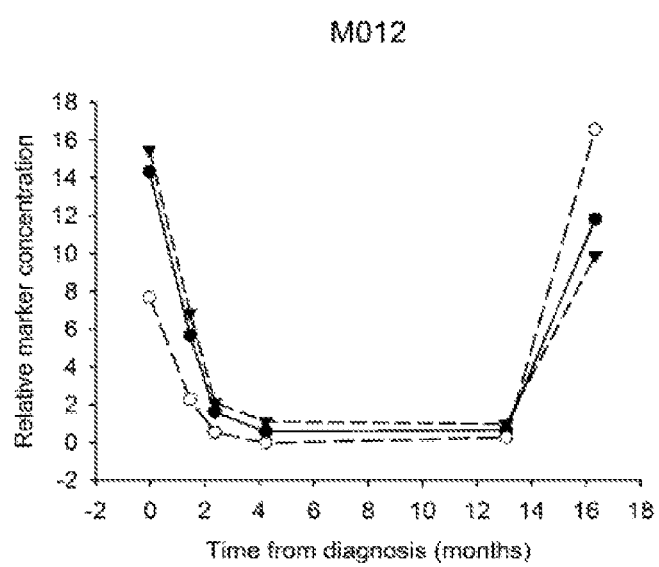

FIG. 14 demonstrates that the present MGL-NP assay shows earlier and stronger relative temporal changes than HE4 and CA125 immunoassays. Each panel represents a different patient and shows relative concentrations of HE4, CA125, and CA125$^{MGL}$ over time.

Figure 15A:
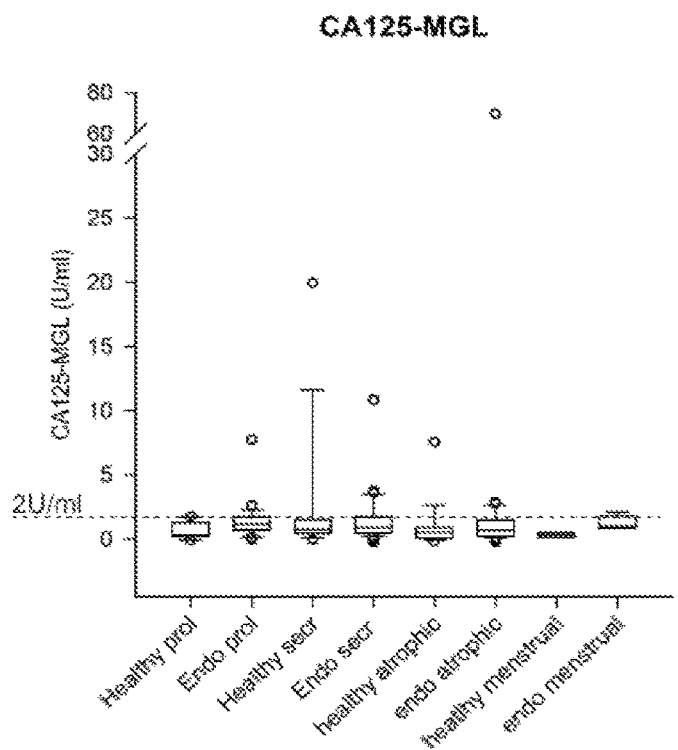
Figure 15B:
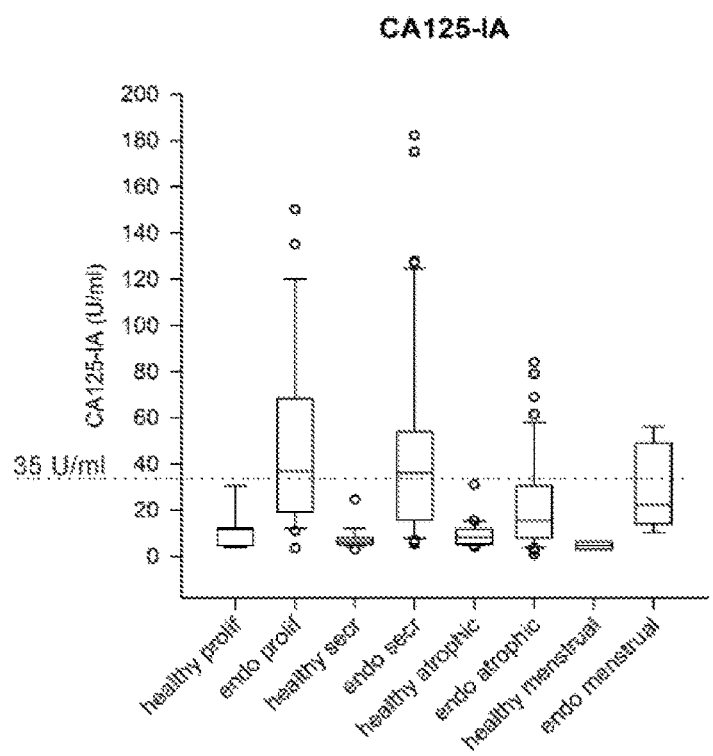
Figure 15C:
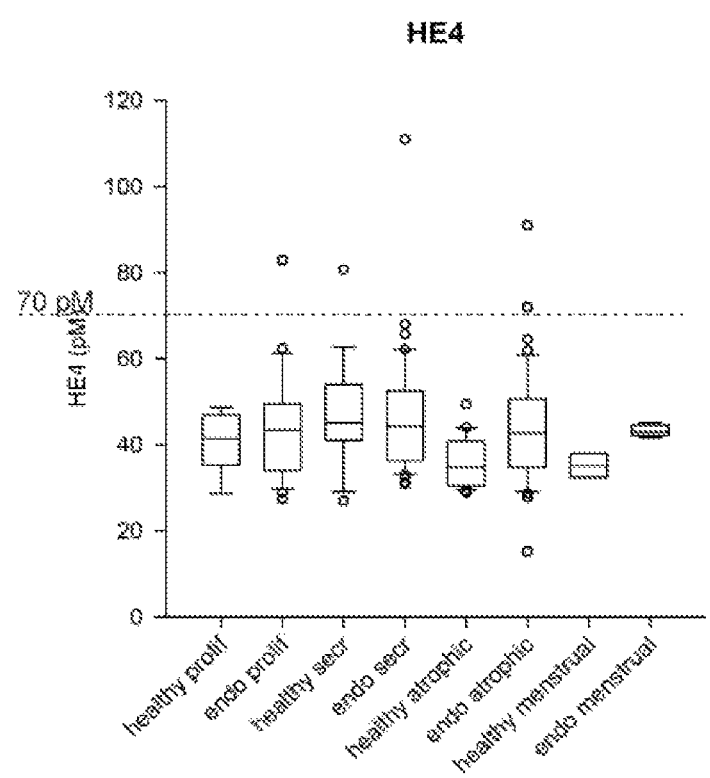

FIGS. 15A to 15C demonstrate that hormonal status does not have any effect on serum levels of CA125$^{MGL}$ and HE4. Boxes represent healthy controls or patients with endometriosis at different stages of the mensuration cycle as indicated. The horizontal broken line shows the cut-off value for the marker in question. Box Plots for CA125 and HE4 were adapted from Hallamaa et al. (Gynecol. Oncol., 2012, 125: 667-672). Abbreviations: prol, prolif, proliferative; secr, secretory; endo, endometriosis; IA, immunoassay.

DETAILED DESCRIPTION OF THE INVENTION

The present disclosure is based on studies aiming to distinguish epithelial ovarian cancer (EOC)-related CA125 from other CA125 species on the basis of CA125 glycosylation pattern. In accordance with this aim, the present disclosure provides means and methods of determining a gynaecological disease state in a subject who is suspected to suffer from or be at risk of suffering from said gynaecological disease, especially for diagnosing, prognosing, or monitoring a gynaecological disease, particularly a gynaecological disease selected from the group consisting of EOC, endometriosis, and endometrial cancer.

As used herein, the term "or" has the meaning of both "and" and "or" (i.e. "and/or"). Furthermore, the meaning of a singular noun includes that of a plural noun and thus a singular term, unless otherwise specified, may also carry the meaning of its plural form. In other words, the term "a" or "an" may mean one or more.

As used herein, the term "subject" refers to an animal, preferably to a mammal, more preferably to a human, and most preferably to a female. Depending on an embodiment in question, said subject may suffer from a gynaecological disease with or without diagnosis, be suspected to suffer from a gynaecological disease, be at risk of said gynaecological disease, or may have already been treated for a gynaecological disease. In some preferred embodiments, said gynaecological disease is selected from the group consisting of EOC, endometriosis, and endometrial cancer. In some more preferred embodiments, said gynaecological disease is EOC. Herein, the terms "human subject", "patient" and "individual" are interchangeable.

As used herein, the term "sample" refers to a tissue sample, such as a biopsy sample taken from an ovary or endometrium, and to a sample of a bodily fluid, such as ascites fluid, urine, blood, plasma, serum, and peritoneal cavity fluid, obtained from a subject. In some embodiments, said tissue sample may be a formalin-fixed or paraffin-embedded tissue sample. Generally, obtaining the sample to be analysed from a subject is not part of the present method of determining a subject's gynaecological disease state. A blood, serum or plasma sample is the most preferred sample type to be used in the present method and its all embodiments.

In embodiments which concern assessment of the level of more than one biomarker, same or different samples obtained from a subject whose gynaecological disease state is to be determined may be used for each assessment. Said different samples may be of the same or different type.

As used herein, the term "level" is interchangeable with the terms "amount" and "concentration", unless otherwise indicated.

To determine whether a detected level of a biomarker is indicative of the presence or risk of a disease associated with said biomarker, its level in a relevant control has to be determined. Once the control levels are known, the determined marker levels can be compared therewith and the significance of the difference can be assessed using standard statistical methods. In some embodiments, a statistically significant difference between the determined biomarker level and the control level is indicative of the disease in question. In some further embodiments, before to be compared with the control, the biomarker levels are normalized using standard methods.

As used herein, the term "control" may refer to a control sample obtained from an apparently healthy individual or pool of apparently healthy individuals, or it may refer to a predetermined threshold value, i.e. a cut-off value, which is indicative of the presence or absence of the disease in question. Statistical methods for determining appropriate threshold values will be readily apparent to those of ordinary skill in the art. The threshold values may have been determined, if necessary, from samples of subjects of the same age, demographic features, and/or disease status, etc. The threshold value may originate from a single individual not affected by the disease in question or be a value pooled from more than one such individual. Non-limiting examples of suitable predetermined threshold values include, but are not limited to, 35 U/ml for CA125, and 70 pM for HE4, as is generally accepted.

In the cohorts studied in the experimental part, almost 90% of healthy women showed a CA125$^{MGL}$ concentration below 2 U/ml, while only 4 among 51 healthy women tested showed a $CA125^{MGL}$ concentration >2 U/ml. Thus, in some embodiments the predetermined threshold value for $CA125^{MGL}$ may be from about 2 U/ml to about 3 U/ml, e.g. about 2 U/ml or about 2.8 U/ml. However, depending on the desired sensitivity and specificity, other predetermined threshold values for $CA125^{MGL}$ may be used. Non-limiting examples of such other threshold values include any values falling within ranges from about 2 U/ml to about 7 U/ml, from about 2 U/ml to about 6 U/ml, from about 2 U/ml to about 5 U/ml, and from about 2 U/ml to about 4 U/ml. For screening purposes and other uses where the clinical sensitivity of the assay needs be maximized, threshold values as low as about 0.5 to 2 U/ml, e.g. about 1 U/ml or 1.5 U/ml, may also be used. On the other hand, in diagnostic or other embodiments where the clinical specificity of the assay needs be maximized, threshold values as high as about 5 to 20 U/ml, e.g. about 10 U/ml or 15 U/ml, may also be used. However, these ranges may also vary depending on the specifics of the detection technique or means to provide MGL in high enough avidity into the assay.

In some embodiments, the term "control sample" refers to a sample obtained from the same subject whose gynaecological disease state is to be determined but obtained at a time point different from the time point of the disease state determination. Non-limiting examples of such different time points include one or more time points before diagnosis of the disease, one or more time points after diagnosis of the disease, one or more time points before treatment of the disease, one or more time points during treatment of the disease, and one or more time points after treatment of the disease. Typically, such control samples obtained from the same subject are used when the purpose of the gynaecological disease state determination is to monitor said disease, especially to monitor the onset of the disease, or risk development of the disease, response to treatment, relapse of the disease, or recurrence of the disease.

As used herein, the term "apparently healthy" refers to an individual or a pool of individuals who show no signs of a disease in question and thus are believed not to be affected by said disease in question or who are predicted not to develop said disease in question.

As used herein, the term "indicative of a disease", when applied to a biomarker, refers to a level which, using routine statistical methods setting confidence levels at a minimum of 95%, is diagnostic of said disease or a stage of said disease such that the detected level is found significantly more often in subjects with said disease or a stage of said disease than in subjects without said disease or another stage of said disease. Preferably, the level which is indicative of a disease is found in at least 80% of subjects who have the disease and is found in less than 10% of subjects who do not have the disease. More preferably, the level which is indicative of said disease is found in at least 90%, at least 95%, at least 98%, or more in subjects who have the disease and is found in less than 10%, less than 8%, less than 5%, less than 2.5%, or less than 1% of subjects who do not have the disease.

Existing CA125 immunoassays routinely used diagnostically are based on the determination of CA125 protein levels in serum or plasma by two different monoclonal antibodies which recognize different protein epitopes of CA125. Such conventional immunoassays, herein referred to as "assaying a sample for CA125 protein concentration", are commercially available from several different providers. Accordingly, the term "CA125" refers to the protein component of CA125 irrespective of its glycosylation pattern. In general, a CA125 serum concentration of 35 U/ml or below is considered normal. However, CA125 concentrations above this cut-off level are frequently found in patients with conditions other than ovarian cancer such as endometriosis, which causes false positive results in EOC diagnostics.

In accordance with this generally accepted flaw of CA125 immunoassays, no discrimination between epithelial ovarian cancer-related CA125 and normal or benign CA125 derived from placental homogenates, amniotic fluid, liver cirrhotic ascites or immature teratoma-related ascites was achieved herein as described in more detail in Example 2.

CA125 is a heavily glycosylated molecule with abundant N-linked and O-linked glycan side chains and an overall carbohydrate content of 24% to 28%. Lectins, i.e. members of a well-known family of carbohydrate-binding proteins that are highly specific for given glycans on the basis of their sugar moiety structures and sequences, have been suggested for identifying changes in the glycosylation of cancer cells and tissues.

Therefore, a panel of plant and human lectins was used in an anti-CA125 antibody-lectin sandwich assay described in more detail in Example 3. According to the results, none of the lectins employed was able to discriminate between normal CA125 derived from amniotic fluid or normal placenta and ovarian cancer-related CA125 derived from a primary ovarian carcinoma cell line called OVCAR-3.

Unexpectedly, however, excellent discrimination between EOC-related and non-EOC-related CA125 was achieved with macrophage galactose-type lectin (MGL) when it was immobilized on a nanoparticle. As demonstrated in Example 3, the present method discriminates EOC-related CA125 from normal/benign CA125 with a minimum of 10-fold preference over placental CA125. The ability of the present method to distinguish EOC-related CA125 from pregnancy-related or endometriosis-related CA125 was verified with clinical serum samples. These results are not limited to the use of MGL when immobilized on a nanoparticle but apply to embodiments, wherein adequate avidity effect and signal amplification are obtained by other techniques.

As used herein, the term "$CA125^{MGL}$" refers to a glycoform of CA125, which binds to MGL, such as nanoparticle-immobilized MGL (MGL-NP), specifically.

As used herein, the term "MGL" refers to an isolated human macrophage galactose-type lectin, which is a C-type lectin receptor (CLR) that is naturally present on our immune cells, more specifically dendritic cells and macrophages. The human MGL has an exclusive specificity for rare terminal GalNAc structures, which are revealed on tumor-associated mucin MUC1. The term "MGL" also encompasses MGL fused at the C-terminus to human IgG1-Fc (MGL-Fc) according to standard methods known in the art. Such MGL-Fc is commercially available. MGL is also known by the names CD301, and C-type lectin domain family 10 member A (CLEC10A). Recombinant human CLEC10A without any Fc fusion is commercially available.

In accordance with the above, the present invention provides a method of determining a gynaecological disease state in a subject by assaying a sample obtained from said subject for $CA125^{MGL}$. Increased level of $CA125^{MGL}$ in said sample as compared with that of a control sample or a predetermined threshold value is indicative that said subject has or is at risk of having EOC. On the other hand, non-increased or normal level of $CA125^{MGL}$ in said sample as compared with that of a control sample or a predetermined threshold value is indicative that said subject is apparently healthy with respect to EOC or is not at risk of having or developing EOC. In some embodiments said method may be a method of determining EOC disease state in a subject. In some further embodiments said method may be a method of diagnosing, prognosing, or monitoring EOC, wherein monitoring EOC encompasses, but is not limited to, monitoring onset of EOC, monitoring any development in risk of EOC, monitoring response to treatment, monitoring relapse of EOC, and monitoring recurrence of EOC.

However, non-increased or normal level of $CA125^{MGL}$ as a test result does not exclude the possibility that the subject whose gynaecological disease state is to be determined may suffer from or be at risk of having a gynaecological disease other than EOC, such as endometriosis or endometrial cancer. On the other, a subject with such a test result may also be apparently healthy with respect not only to EOC, but also to endometriosis and endometrial cancer. Thus, if the purpose of the present method is not only determine a subject's EOC state but to determine a subject's disease state also with respect to other gynaecological diseases such as endometriosis or endometrial cancer, and if level of $CA125^{MGL}$ is non-increased in said sample, further diagnostic testing may be warranted to determine the risk of said subject having a gynaecological disease other than EOC. As set forth below, such further testing may comprise assaying a sample obtained from said subject also for CA125 and/or HE4 in order to determine the risk of said subject having endometriosis or endometrial cancer. Alternatively or in addition, said further testing may also include use of any appropriate diagnostic methods available in the art.

In some embodiments, the method of determining a gynaecological disease state in a subject may be used for differential diagnostics between EOC and endometriosis or endometrial cancer.

As indicated above, the level of $CA125^{MGL}$ in a sample may in some embodiment be quantified or assayed by determining the level of CA125 binding to nanoparticle-immobilized MGL (MGL-NP), for instance by using any assay format exemplified herein. Although the present disclosure focuses on MGL-NP-based assays, other techniques for determining the level of $CA125^{MGL}$ in sample are envisaged as well. In other words, nanoparticles are only one preferred way of providing adequate avidity effect and signal amplification for carrying out the present method and its various embodiments.

As used herein, the term "nanoparticle" (NP) refers to a particle, synthetic or natural, having one or more dimensions, e.g. a diameter, of less than about 1000 nm, e.g. about 500 nm or less, about 100 nm or less, or about 50 nm or less. As used herein, the term "about" refers to a range of values ±10% of a specified value. For example, the phrase "about 100 nm" includes ±10% of 100 nm, or from 90 nm to 110 nm. The nanoparticles may generally have a spherical shape but also non-spherical shapes such as ellipsoidal shapes can be used. In some embodiments, all the dimensions of said nanoparticle are less than about 1000 nm, about 500 nm or less, about 100 nm or less, or about 50 nm or less.

A variety of different materials may be utilized in the present nanoparticles. Non-limiting examples of suitable polymers include poly(ethylene glycol) (PEG), polystyrene, polyethylene, poly(acrylic acid), poly(methyl methacrylate) (PMMA), polysaccharides, and copolymers or combinations thereof. Other suitable nanoparticle materials include, but are not limited to, colloidal gold, silver, quantum dots, carbon, porous silicon, and liposomes. Further suitable nanoparticle materials include protein nanoparticles, mineral nanoparticles, glass nanoparticles, nanoparticle crystals, metal nanoparticles, and plastic nanoparticles.

Nanoparticles suitable for use in the present method may be directly or indirectly qualitatively or quantitatively detectable by any known means. For instance, the nanoparticles may be detectable owing to an inherent quality as in the case of e.g. upconverting nanoparticles (UCNP), resonance particles, quantum dots, and gold particles. In some other embodiments, the nanoparticles can be made detectable e.g. by fluorescent labels, bioluminescent labels, chemiluminescent labels. In some further embodiments, labelling or doping with lanthanides, i.e. luminescent lanthanide ions with luminescence emission in visible or near-infrared or infrared wavelengths and long fluorescence decay, such as europium (Ill), terbium (Ill), samarium (Ill), dysprosium (Ill), ytterbium (Ill), erbium (Ill) and neodynium (Ill), are preferred means for making the present nanoparticles detectable.

In some non-limiting embodiments, the most preferred nanoparticles are polystyrene nanoparticles having a diameter of either 97 nm or 107 nm. Such nanoparticles are commercially available at least from Thermo Scientific Seradyn Inc.

MGL may be immobilized on nanoparticles by any suitable method known in the art, including but not limited to that disclosed in Example 1. Herein, nanoparticle-immobilized MGL is called MGL-NP for short.

Binding of CA125 to MGL-NP may be determined by various ways. In some embodiments, said binding is determined by a sandwich assay wherein a CA125-specific monoclonal antibody is used as a capturing agent and MGL-NP as a tracer. In some other embodiments, the sandwich assay may be conducted using a reversed way. In such cases, MGL-NP is used as a capturing agent and a CA125-specific monoclonal antibody as a tracer. Since urine contains less interfering glycosylated molecules than blood, the reversed sandwich assay may operate better with urine samples than with blood samples.

In some further embodiments of the present MGL-NP assay, mesothelin, a glycosylphosphatidylinositol-linked glycoprotein, may be used instead of a CA125-specific monoclonal antibody either as a capturing agent or as a tracer.

Sandwich assays according to various embodiments of the present invention may be performed either on a solid surface, such as a microtiter plate, or in lateral flow format. Means and methods for binding a capturing agent to a solid surface, e.g. via a streptavidin-biotin complex, or incorporating a capturing agent to a lateral flow assay are known in the art and readily apparent to a skilled person. Any tracer may have been labelled with a detectable label such as a lanthanide chelate selected from europium(III), terbium(III), samarium(III), and dysprosium(III). In some specific embodiments, europium chelate is used as a detectable label. In a non-limiting preferred embodiment, MGL-NP is used as a tracer and is doped with 30000 Eu-chelates. In some other specific embodiments, MGL is attached on upconverting phosphorus (UCP) particles, which are particularly suitable for use as tracers in the lateral flow format.

Any monoclonal anti-CA125 antibody may be used in the abovementioned sandwich assays. Non-limiting examples of suitable commercial anti-CA125 antibodies include Ov185, Ov197, and OvK95, available at least from Fujirebio Diagnostics, Sweden. Further CA125-specific monoclonal antibodies may be produced according to methods well known in the art.

Suitable substrates for use in the present MGL-NP assay include, but are not limited to, glass, silica, aluminosilicates, borosilicates, metal oxides such as alumina and nickel oxide, gold, various clays, nitrocellulose or nylon. In some embodiments, the substrate may be coated with a compound to enhance binding of the anti-CA125 antibody to the substrate. In some further embodiments, one or more control antibodies are also attached to the substrate.

Receiver Operating Characteristic (ROC) curves may be utilized to demonstrate the trade-off between the sensitivity and specificity of a marker, as is well known to skilled persons. The sensitivity is a measure of the ability of the marker to detect the disease, and the specificity is a measure of the ability of the marker to detect the absence of the disease. The horizontal X-axis of the ROC curve represents 1-specificity, which increases with the rate of false positives. The vertical Y-axis of the curve represents sensitivity, which increases with the rate of true positives. Thus, for a particular cut-off selected, the values of specificity and sensitivity may be determined. In other words, data points on the ROC curves represent the proportion of true-positive and false-positive classifications at various decision boundaries. Optimum results are obtained as the true-positive proportion approaches 1.0 and the false-positive proportion approaches 0.0. However, as the cut-off is changed to increase specificity, sensitivity usually is reduced and vice versa.

As used herein, the term "false positive" refers to a test result, which classifies an unaffected subject incorrectly as an affected subject. Likewise, "false negative" refers to a test result, which classifies an affected subject incorrectly as an unaffected subject.

As used herein, the term "true positive" refers to a test result, which classifies a subject who has a disease correctly as an affected subject. Likewise, "true negative" refers to a test result, which classifies an unaffected subject correctly as an unaffected.

In accordance with the above, the term "success rate" refers to the percentage-expressed proportion of affected individuals with a positive result, while the term "false positive rate" refers to the percentage-expressed proportion of unaffected individuals with a positive result.

The area under the ROC curve, often referred to as the AUC, is a measure of the utility of a marker in the correct identification of disease subjects. Thus, the AUC can be used to determine the effectiveness of the test. An area of 1 represents a perfect test; an area of 0.5 represents a worthless test. A traditional rough guide for classifying the accuracy of a diagnostic or predictive test is the following: AUC values 0.9 to 1 represent test with excellent diagnostic or prognostic power, AUC values 0.80 to 0.90 represent a test with good diagnostic or prognostic power, AUC values 0.70 to 0.80 represent a test with fair diagnostic or prognostic power, AUC values 0.60 to 0.70 represent a test with poor diagnostic or prognostic power, and AUC values 0.50 to 0.60 represent a test with failed diagnostic or prognostic power.

As shown in the experimental part, depending on the EOC patient group employed (all 213 EOC cases, 43 cases representing early stages of EOC, or 29 cases representing advanced stages of EOC), present MGL-NP assay was able to distinguish EOC from endometriosis with AUC values of 0.815, 0.870 or 0.899. The success rate of the present MGL-NP assay in the clinical cohort representing early progression/relapse stages of EOC was 71.9%.

The above values were improved when the MGL-NP assay was combined with the conventional CA125 immunoassay, which determines the overall serum concentration of CA125 protein irrespective of its glycoform composition. The success rate of the combined determination of $CA125^{MGL}$ and CA125 in the clinical cohort representing early stages of EOC was improved to 81.2%. Thus, in some embodiments, the present method of determining a subject's gynaecological disease state may comprise determination of levels of both $CA125^{MGL}$ and CA125 in a sample obtained from said subject, preferably in a blood sample, more preferably in serum or plasma. Such a combined determination would at least in some cases improve the accuracy of the test result or confirm it.

Combined determination of the level of both $CA125^{MGL}$ and CA125 is particularly useful for distinguishing subjects having or being at risk of EOC and subjects having or being at risk of endometriosis from each other, i.e. for differential diagnostics of between EOC and endometriosis. This is at least partly because while having excellent ability to detect EOC-related CA125, $CA125^{MGL}$ does not distinguish apparently healthy subjects from those suffering from endometriosis, because $CA125^{MGL}$ concentration is not increased in samples obtained from subjects with endometriosis. In other words, normal or non-increased level of $CA125^{MGL}$ does not tell whether the subject is apparently healthy with respect to endometriosis or has or is at risk of having endometriosis. CA125 protein concentration, in turn, typically increases both in EOC and endometriosis. Thus, increased concentration of both $CA125^{MGL}$ and CA125 is indicative of the presence or risk of EOC, while non-increased level of $CA125^{MGL}$ with concomitantly increased CA125 protein concentration is indicative of the presence or risk of endometriosis. On the other hand, non-increased concentration of both $CA125^{MGL}$ and CA125 is indicative of the presence or risk of neither EOC nor endometriosis.

Accordingly, in some embodiments, the present method of determining a gynaecological disease state may be a method of determining EOC disease state in a subject, such as a method of diagnosing, prognosing, or monitoring EOC in a subject, wherein the method comprises assaying a sample obtained from said sample for $CA125^{MGL}$, and assaying the same or a different sample obtained from said subject for CA125 protein concentration. In such a method, increased level of $CA125^{MGL}$ in combination with increased CA125 protein concentration would be indicative that said subject has or is at risk of having EOC. On the other hand, non-increased or normal level of $CA125^{MGL}$ in combination with non-increased or normal CA125 protein concentration would be indicative that said subject does not have or is not at risk of having EOC, i.e. is apparently healthy with respect to EOC.

In some other embodiments, the method may be a method of determining endometriosis disease state in subject, such as a method of diagnosing, prognosing or monitoring endometriosis, wherein the method comprises assaying a sample obtained from said sample for $CA125^{MGL}$, and assaying the same or a different sample obtained from said subject for CA125 protein concentration. In such a method, non-increased level of $CA125^{MGL}$ in combination with increased CA125 protein concentration would be indicative that said subject has or is at risk of having endometriosis. On the other hand, non-increased level of $CA125^{MGL}$ in combination with non-increased CA125 protein concentration would be indicative that said subject does not have or is not at risk of having endometriosis, i.e. is apparently healthy with respect to endometriosis.

As shown in the experimental part, the performance of the MGL-NP assay for distinguishing subjects with EOC from subjects with endometriosis, was also improved by a combined use with a conventional HE4 immunoassay. HE4 (human epididymis protein 4) is a known serum biomarker, which is overexpressed in both ovarian and endometrial cancers. The success rate of the combined determination of $CA125^{MGL}$ and HE4 in the clinical cohort representing early stages of EOC was improved to 93.7%. Thus, in some embodiments, the present method of determining a subject's gynaecological disease state may comprise determination of levels of both $CA125^{MGL}$ and HE4, preferably in blood, more preferably in serum or plasma. In any of the embodiments of the present method which involve HE4 measurements, suitable predetermined threshold values for comparing with the detected HE4 concentration include, but are not limited to, 70 pM, especially for pre-menopausal subjects or subjects under the age of 50, and 90 pM or 140-150 pM, especially for postmenopausal subjects or subjects above the age of 50.

Accordingly, in some embodiments, determination of serum levels of both $CA125^{MGL}$ and HE4 may be used for determining EOC disease state in a subject, more specifically for diagnosing, prognosing or monitoring EOC in said subject. In such a method, increased concentration of both $CA125^{MGL}$ and HE4 would be indicative of the presence or risk of EOC, while non-increased concentration of both $CA125^{MGL}$ and HE4 would indicate that said subject does not have or is not at risk of having EOC, i.e. is apparently healthy with respect to EOC.

In some other embodiments, determination of serum levels of both $CA125^{MGL}$ and HE4 may be used for differential diagnostics of EOC and endometrial cancer. In such a method, increased concentration of both $CA125^{MGL}$ and HE4 would be indicative of the presence or risk of EOC, while non-increased concentration of $CA125^{MGL}$ with concomitantly increased concentration of HE4 would be indicative of the presence or risk of endometrial cancer.

In some further embodiments, determination of serum levels of both $CA125^{MGL}$ and HE4 may be used for determining endometrial cancer disease state in a subject, more specifically for diagnosing, prognosing or monitoring endometrial cancer in said subject. In such a method, non-increased concentration of $CA125^{MGL}$ with concomitant increase in HE4 concentration would indicate that said subject has or is at risk of endometrial cancer, while non-increased concentration of both $CA125^{MGL}$ and HE4 subject would indicate that said subject does not have or is not at risk of having endometrial cancer, i.e. is apparently healthy with respect to endometrial cancer.

In some further embodiments, $CA125^{MGL}$, CA125, and HE4 may all be used in combination for determining a subject's a gynaecological disease state, especially concerning a disease selected from EOC, endometriosis, and endometrial cancer, for differential diagnostics between EOC, endometriosis and endometrial cancer, and for any diagnostic, prognostic and/or monitoring purpose concerning EOC, endometriosis and endometrial cancer.

As shown in the Examples below, the combined use of the three biomarkers provided an excellent discrimination of EOC from endometriosis. To be more specific, AUC values of 0.899, 0.947, and 0.967 were obtained in the group of non-categorized EOC samples (n=213), the group of serum samples representing early stages of EOC (n=43) and the group of serum samples representing advanced stages of EOC (n=29), respectively. Thus, in some embodiments provided is a method of determining a subject's EOC disease state, such as a method of diagnosing, prognosing, or monitoring EOC in said subject, by assaying same or different samples for concentrations of $CA125^{MGL}$ CA125, and HE4 in said sample. In such methods, concomitantly increased concentration of $CA125^{MGL}$, CA125, and HE4 would be indicative of said subject having or being at risk of having EOC. On the other hand, concomitantly non-increased concentrations of $CA125^{MGL}$, CA125, and HE4 would be indicative of said subject not having or not being at risk of having EOC.

In some further embodiments provided is a method of determining a subject's endometriosis state, such as a method of diagnosing, prognosing, or monitoring endometriosis in said subject, by assaying same or different samples for concentrations of $CA125^{MGL}$, CA125, and HE4 in said sample. In such methods, increased concentration of CA125 in combination with concomitantly non-increased concentration of $CA125^{MGL}$ and HE4 would be indicative of said subject having or being at risk of having endometriosis. On the other hand, concomitantly non-increased concentrations of $CA125^{MGL}$, CA125, and HE4 would be indicative of said subject not having or not being at risk of having endometriosis.

In some still further embodiments provided is a method of determining a subject's endometrial cancer state, such as a method of diagnosing, prognosing, or monitoring endometrial cancer in said subject, by assaying same or different samples for concentrations of $CA125^{MGL}$, CA125, and HE4 in said sample. In such methods, increased concentration of HE4 in combination with concomitantly non-increased concentration of $CA125^{MGL}$ and CA125 would be indicative of said subject having or being at risk of having endometriosis. On the other hand, concomitantly non-increased concentrations of $CA125^{MGL}$, CA125, and HE4 would be indicative of said subject not having or not being at risk of having endometrial cancer.

Furthermore, various embodiments of the present method may be used for differential diagnostics between gynaecological diseases selected from the group consisting of EOC, endometriosis, and endometrial cancer, and other diseases associated with abdominal pain including, but not limited to, colon cancer, ulcerative colitis, irritable bowel disease, irritable bowel syndrome and Crohn's disease.

As set forth above, the present method is in some embodiments directed to diagnosing of a gynaecological disease, including EOC, endometriosis, and endometrial cancer, i.e. determining whether or not a subject has or is at risk of said gynaecological disease. This is also meant to include instances where the presence or the risk of the gynaecological disease is not finally determined but that further diagnostic testing is warranted. In such embodiments, the method is not by itself determinative of the presence or absence, or of the risk of the gynaecological disease in the subject but can indicate that further diagnostic testing is needed or would be beneficial. Therefore, the present method may be combined with one or more other diagnostic methods for the final determination of the presence or absence, or of the risk of the gynaecological disease in the subject. Such other diagnostic methods are well known to a person skilled in the art.

Being non-invasive and suitable for analysing serum samples, the present method and its various embodiments may be easily incorporated into a population screening protocol to identify subjects having or being at risk of having or developing EOC, endometriosis, or endometrial cancer. This would enable not only early diagnosis of EOC, endometriosis, or endometrial cancer, but also active surveillance for the onset of EOC, endometriosis, or endometrial cancer in subjects with identified increased risk of developing EOC, endometriosis, or endometrial cancer later in life. Moreover, early detection of EOC, endometriosis, or endometrial cancer would allow treating the disease early when chances of cure are at their highest.

The present method and its various embodiments may be used not only for diagnostic purposes but also for prognosis or predicting the outcome of a gynaecological disease, including EOC, endometriosis, and endometrial cancer, or monitoring the subject's recovery or survival from said gynaecological disease, any possible relapse or recurrence of the disease or response to treatment. In some embodiments, the method comprises monitoring said gynaecological disease state of said subject by comparing the levels of CA125 binding to said MGL-NP or the amount of $CA125^{MGL}$, with or without concomitantly comparing the levels of one or both of HE4 and CA125, at different time points after diagnosis of the gynaecological disease in question and/or before, during, and after therapeutic intervention, e.g. by surgery, radiation therapy, chemotherapy, any other suitable therapeutic treatment, or any combination thereof, to relieve or cure the gynaecological disease in question. In some other embodiments, the method comprises determining said subject as having relapse or recurrence of EOC or as being at risk of relapse or recurrence of EOC, if the level of CA125 binding to said MGL-NP or the amount of $CA125^{MGL}$ is higher than in a control or above a predetermined threshold value.

In some embodiments, diagnosing, prognosing and/or monitoring EOC, as set forth herein, are all encompassed by the expression "determining an EOC disease state", be it de novo or recurrent appearance or suspicion of EOC. Thus, the present method may be formulated as a method of determining an EOC disease status in a subject suspected of suffering from EOC, comprising assaying the level of CA125 which binds to MGL-NP or the level of $CA125^{MGL}$ in a sample obtained from said subject, and determining the EOC disease status in said subject on the basis of said level of CA125 which binds to MGL-NP or said level of $CA125^{MGL}$. In other words, the method of diagnosing, prognosing, and/or monitoring EOC in a subject suspected of suffering from or being at risk of EOC, may comprise assaying the level of CA125 which binds to MGL-NP or the level of $CA125^{MGL}$ in a sample obtained from said subject, and diagnosing, prognosing, and/or monitoring EOC in said subject on the basis of said level of CA125 which binds to MGL-NP or said level of $CA125^{MGL}$ In such methods, increased level of CA125 which binds to MGL-NP or increased level of $CA125^{MGL}$ as compared to a relevant control or a predetermined threshold value is indicative of the presence of EOC, or of a risk of EOC.

Comparison of the level of CA125 binding to MGL-NP or the level of $CA125^{MGL}$ in sample to be analysed with that of a relevant control or a predetermined threshold value may in some embodiments be performed by a processor of a computing device. Regardless of whether or not the processor of the computing device is used for said comparison, the level of CA125 binding to MGL-NP or the amount of $CA125^{MGL}$ is, at least in some embodiments, determined as "increased" or "higher" if the level of CA125 binding to MGL-NP or the amount of $CA125^{MGL}$ in the sample is, for instance, at least about 1.5 times, 1.75 times, 2 times, 3 times, 4 times, 5 times, 6 times, 8 times, 9 times, 10 times, 20 times or 30 times the predetermined threshold level, or the level of CA125 binding to MGL-NP or the amount of $CA125^{MGL}$ in the control sample. In some embodiments, the difference between the level of CA125 binding to MGL-NP or the amount of $CA125^{MGL}$ in the sample to be analyzed and the predetermined threshold level, or the level of CA125 binding to MGL-NP or the amount of $CA125^{MGL}$ in the control sample has to be statistically significant in order to provide a proper diagnostic, prognostic or predictive result.

"Increased" concentration of HE4 or CA125 may be defined correspondingly, as is apparent to those skilled in the art.

Concentration of $CA125^{MGL}$, CA125 or HE4 in a sample obtained from a subject whose gynaecological disease state is to be determined or who is to be diagnosed, prognosed, or monitored for a gynaecological disease is considered "non-increased" or "normal" if the detected concentration thereof is lower, essentially the same or essentially non-altered as compared with that of a relevant control sample or a predetermined threshold value.

In some embodiments, the present method is particularly suitable for early diagnosis of EOC and early detection of EOC relapse, recurrence and progression. Likewise, $CA125^{MGL}$ may serve as an early tumor marker for EOC as well as for EOC relapse, recurrence and/or progression. Thus, the present method and $CA125^{MGL}$ may be used not only for diagnostic, prognostic and monitoring purposes but also for screening of asymptomatic women for EOC or a risk of developing EOC.

The present disclosure also provides a kit for use in the present method and its various embodiments. The kit comprises a CA125 binding agent, such as a monoclonal anti-CA125 antibody or mesothelin, and nanoparticles onto which MGL has been immobilized. Either said CA125 binding agent or MGL-NP comprises a detectable label, and may have been immobilized on a solid surface, such as a microtiter plate. Various details and embodiments of the present method apply also to the present kit, as is readily understood by a skilled person. Thus, properties and features of suitable nanoparticles, for instance, are not repeated herein.

In some embodiments, said anti-CA125 antibody has been attached onto a solid surface, such as a microtiter plate. In some further embodiments, streptavidin coating of the plates and biotinylation of the antibody are used for said attaching. Alternative ways of achieving the same are readily available for a skilled person.

Optionally, the kit may also comprise a control for comparing to a measured value of CA125 binding to MGL-NP. In some embodiments, the control is a threshold value for comparing to the measured value.

In some embodiments, the kit may further comprise one or more reagents for assaying CA125 and/or HE4 protein concentration. Non-limiting examples of typical reagents for assaying CA125 protein concentration include two CA125 binging agents, such as two monoclonal anti-CA125 antibodies, which bind to different protein epitopes in CA125. One of the CA125 binding agents may be the same as the CA125 binding agent provided for assaying $CA125^{MGL}$. Non-limiting examples of typical reagents for assaying HE4 protein concentration include two HE4 binging agents, such as two monoclonal anti-HE4 antibodies, which bind to different protein epitopes in HE4. One of the two CA125 or HE4 binding agents may be immobilized on a solid surface while the other CA125 or HE4 binding agent may comprise a detectable label.

In some further embodiments, the kit may also comprise a computer readable medium comprising computer-executable instructions for performing any method of the present disclosure.

Embodiments of the kit which contain reagents for assaying samples for the concentration of $CA125^{MGL}$ and preferably also for CA125 and/or HE4 may also comprise reagents for assaying said samples for any other biomarker, especially for one or more biomarkers associated with any disease other than EOC, endometriosis, or endometrial cancer, such as other gynaecological diseases or diseases associated with lower abdominal pain. Thus, the kit may be used not only for diagnosing, prognosing, or monitoring EOC, endometriosis, and/or endometrial cancer but also for diagnosing, prognosing, or monitoring, for example, other gynaecological diseases or other diseases associated with lower abdominal pain, depending on the specificity and sensitivity of the one or more other biomarkers whose concentrations are to be assayed.

Also provided are herein-disclosed nanoparticles comprising immobilized MGL (MGL-NP); a composition comprising said MGL-NP; use of MGL, said MGL-NP, or said composition for determining a state of a gynaecological disease, especially a gynaecological disease selected from the group consisting of EPC, endometriosis, and endometrial cancer, in a subject; use of MGL, said MGL-NP, or said composition for diagnosing, prognosing, or monitoring a gynaecological disease in a subject; use of MGL, said MGL-NP, or said composition for diagnosing, prognosing, or monitoring EOC in a subject; use of MGL, said MGL-NP, or said composition for diagnosing, prognosing, or monitoring endometriosis in a subject; use of MGL, said MGL-NP, or said composition for diagnosing, prognosing, or monitoring endometrial cancer in a subject; use of MGL, said MGL-NP, or said composition for differential diagnostics of EOC, endometriosis, or endometrial cancer; use of MGL, said MGL-NP, or said composition for differentiating EOC, endometriosis, or endometrial cancer from other diseases associated with lower abdominal pain, such as colon cancer, ulcerative colitis, irritable bowel disease, irritable bowel syndrome and Crohn's disease. In some embodiments, said uses of MGL, said MGL-NP, or said composition may require concomitant use of reagents or methods for determination of HE4 and/or CA125 protein concentration to achieve the desired diagnostic or prognostic effect, or to enable monitoring the onset, progression, relapse, or recurrence of the disease in question, or response to treatment. Any details and applications disclosed with respect to the present method and its embodiments apply to the various uses of MGL-NP even though the details and applications are not repeated herein.

It will be obvious to a person skilled in the art that, as technology advances, the inventive concept can be implemented in various ways. The invention and its embodiments are not limited to the examples described below but may vary within the scope of the claims.

EXAMPLES

Example 1: Materials and Methods

Origins of CA125 and Clinical Samples

Purified CA125 from a primary ovarian carcinoma (OvCa) cell line, OVCAR-3, was obtained from Fujirebio Diagnostics, Sweden. In the present experiments, said OVCAR-3-derived CA125 antigen was used to represent malignant CA125 because it is the only antigen studied in detail (cloning, glycosylation, interactions).

All biological samples were provided by Department of Pathology, University of Turku, Finland with appropriate permissions and informed consents in accordance with the ethical guidelines of the Hospital District of Southwest Finland.

Initially, normal amniotic fluid and placental homogenate supernatant were used as non-malignant (i.e. normal) sources of CA125. Later, ascites fluids of liver cirrhosis patients (LC) and immature teratoma (germ line ovary cancer different from EOC; IT) were included as additional sources of CA125. The content of CA125 in each sample was determined by a conventional CA125 immunoassay using purified OVCAR-3 derived CA125 as a standard.

Archived serum samples (n=401) with four different clinical statuses as indicated in Table 1 were also employed.

TABLE 1

Clinical serum samples

| Clinical status | Number of serum samples (n = 401) |
|---|---|
| Epithelial ovarian cancer, sequential samples of 68 patients | 213 |
| Endometriosis (Stage 1-2 and 3-4) | 121 (Stage 1-2 = 33; Stage 3-4 = 88) |
| Healthy Control | 51 |
| Endometrial Cancer | 16 |

Anti-CA125 Antibodies

Three different monoclonal anti-CA125 antibodies, namely Ov185, Ov197 and OvK95, which detect different protein epitopes of CA125 were obtained from Fujirebio Diagnostics (Göteborg, Sweden).

For use as tracers, the antibodies were labelled with $Eu^{3+}$ chelates using standard protocols known in the art.

For use as solid-phase capture agents, the antibodies were biotinylated for 4 h at room temperature (RT) with a 40-fold molar excess of biotin isothiocyanate using a standard procedure known in the art. The biotinylated antibodies were purified with NAP-5 and NAP-10 gel-filtration columns (GE Healthcare, Schenectady, N.Y., USA) by using 50 mmol/L Tris-HCl (pH 7.75), containing 150 mmol/L NaCl and 0.5 g/L $NaN_3$. The labelled antibodies were stabilized with 1 g/L BSA (Bioreba, Nyon, Switzerland) and stored at +4° C.

Lectins

A panel of plant lectins was purchased from VECTOR lab and two human lectins, namely MGL and DC-SIGN, were provided by VU University Medical Center Amsterdam, the Netherlands. The extracellular part of MGL was amplified on pRc/CMV-MGL with PCR, confirmed by sequence analysis and fused at the C-terminus to human IgG1-Fc in the Sig-plgG1-Fc vector. MGL-Fc was produced by transient transfection of CHO cells. In the present examples, MGL-Fc is referred to as MGL.

TABLE 2

Lectins employed in the present experiments

| Lectin name | Major carbohydrate binding specificity |
|---|---|
| SBA (Soy bean agglutinin) | GalNAc α1-Ser/Thr |
| SNA (*Sambucus Nigra* agglutinin) | sialic acid α2,6Gal/GalNAc |
| PNA (Peanut agglutinin) | Galβ1,3GalNAc α1-Ser/Thr |
| MAA (*Maackia amurensis* lectin I) | sialic acid α2,3Gal β1,4GlcAc |
| AAL (*Aleuria aurantia* agglutinin) | Fuc α1,6 GlaNAc |
| UEA (*Ulex europeus* agglutinin) | Fuc α1,2 Gla |
| PHA-E (*Phaseolus vulgaris* agglutinin- erythroagglutinin) | GalNAc β1,4 linked to β-mannosyl residue of the trimannosyl core |
| RCA (*Ricinus communis* agglutinin) | Gal β1,4GlcNAc |
| WGA (Wheat germ agglutinin) | GlcNAc β 1,4 GlcNAc |
| WFA (*Wisteria floribunda* agglutinin) | GAlNAc α or β- 3 or 6 position of galactose |
| PSA (*Pisum sativum* agglutinin) | Mannose α N-acetylchitobiose-linked α-fucose |
| VVL (Vicia villosa lectin) | α- or β-GalNAc linked to serine or threonine in a polypeptide (Tn antigen) |

TABLE 2-continued

Lectins employed in the present experiments

| Lectin name | Major carbohydrate binding specificity |
|---|---|
| TJA-II (*Trichosanthes japonica* agglutinin) | Fuc α 1-2Gal and β-GalNAc |
| MGL (macrophage galactose lectin) | GalNAc linked to serine or threonine in a polypeptide (Tn antigen) |
| DC-SIGN | Nonsialylated Lewis antigen |

Lectins were either labelled with N1 europium chelates or immobilized onto europium chelate-doped, monodisperse, carboxyl-modified FluoroMax™polystyrene nanoparticles (107 nm in diameter, carboxyl content 0.157 mEq/g, parking area 56.6 Å$^2$) which were obtained from Thermo Scientific Seradyn Inc., Indianapolis, Ind.). The nanoparticles employed produce a longlifetime fluorescence equivalent to 30,000 chelated ions per particle.

Primary amino groups of lectins were covalently coupled to activated carboxyl groups of the nanoparticles using a procedure described previously with some minor modifications (Soukka et al., Anal. Chem. 2001, 73, 2254-2260). The nanoparticles (1e10$^{12}$ particles) were suspended in 10 mmol/L phosphate buffer (pH 7.0), and their surfaces were activated with 0.75 mmol/L N-(3-dimethylaminopropyl)-N-ethylcarbodiimide (Sigma-Aldrich, St. Louis, Mo., USA) and 10 mmol/L N-hydroxysulfosuccinimide sodium salt (Sigma-Aldrich). The concentrations of lectins in the coupling reactions were 0.625 mg/ml, and the reactions contained 100 mmol/L NaCl. The activated particles were mixed with the lectins. The coupling reactions were incubated for 2 h at +23° C. with vigorous shaking. Final washes and blocking of the remaining active groups were performed in Tris-based buffer (10 mmol/L Tris, 0.5 g/L NaN$_3$, pH 8.5), and the nanoparticle-lectin conjugates were stored in the same buffer supplemented with 2 g/L BSA at 4° C. Before the first instance of use, the particles were mixed thoroughly, sonicated, and centrifuged lightly (350 g, 5 min) to separate non-colloidal aggregates from the monodisperse suspension.

CA125 Assays

Red assay buffer, wash buffer and streptavidin-coated low-fluorescence microtiter plates used in these experiments were purchased from Kaivogen Oy, Turku, Finland.

Biotinylated solid-phase antibodies (200 ng) were immobilized onto streptavidin-coated microtiter wells in 100 μL of the assay buffer. After 1 h incubation at RT and shaking at 900 rpm, the wells were washed two times with the wash solution and used immediately in the assays.

Next, 50 μl of diluted samples (1:5 in assay buffer) were added to each well, and incubated for 1 h at RT with shaking. CA125 antigens of different origins thereby captured on the wells were used in three different time-resolved fluorescence (TRF) assay formats with three different Eu$^{3+}$-labelled tracers, namely Ov185-Eu$^{3+}$ mAb for detecting the protein epitope of CA125, and either various Eu$^{3+}$-labelled lectins or Eu$^{3+}$-labelled lectin-nanoparticles for detecting the glycan epitope of CA125.

For detecting solid-phase-captured CA125 in a conventional CA125 immunoassay (Example 2), 200 μl of assay buffer containing 25 ng of Ov185-Eu$^{3+}$ mAb was added to each well, and incubated for 1 h at RT with shaking. Time-resolved fluorescence for europium was measured (lex: 340 nm; lem: 615 nm) after adding enhancement solution for 10 min RT with shaking at 900 rpm using Victor3V 1420 Multilabel counter.

For detecting solid-phase-captured CA125 in an anti-CA125 antibody-lectin sandwich assay (Example 3), 200 μl assay buffer containing 25 ng of Eu+3-lectin was added to each well, and incubated for 1 h at RT with shaking. Time-resolved fluorescence for europium was measured (lex: 340 nm; lem: 615 nm) after adding enhancement solution for 10 min RT with shaking at 900 rpm using Victor3V 1420 Multilabel counter.

For detecting solid-phase-captured CA125 in an anti-CA125 antibody-lectin nanoparticle sandwich assay (Example 4), 100 μl of assay buffer containing 5e6 Eu$^{3+}$-NPs coated with various lectins, with additional 6 mM CaCl$_2$ for CLR (DC-SIGN, MGL), was added to each well and incubated for 2 h at RT with shaking. After the incubation, the wells were washed 6 times with the wash buffer. Time-resolved fluorescence for europium was measured (lex: 340 nm; lem: 615 nm) from dry wells using Victor3V 1420 Multilabel counter.

HE4 and CA125 Assays for Clinical Serum Samples

Human epididymis protein (HE4) and CA125 protein concentrations were analyzed in serum samples by ELISA analysis (Fujirebio Diagnostics Inc., Malvern, Pa., USA) according to manufacturer's instructions.

Example 2: Conventional CA125 Immunoassay

Figure 1:
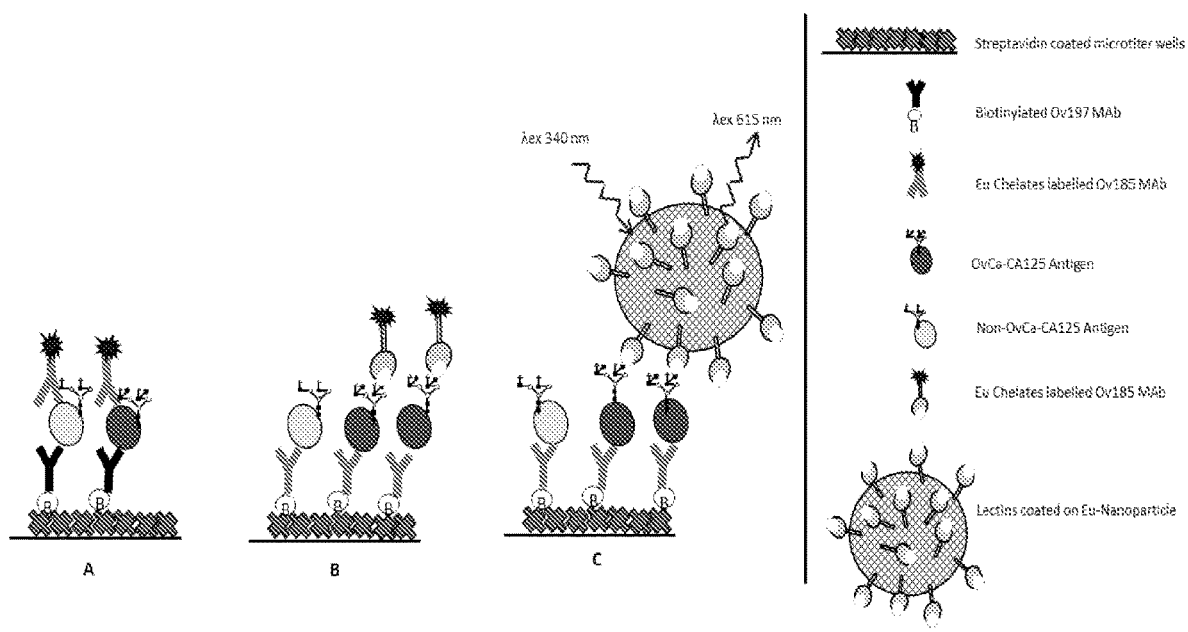
FIG. 1 illustrates the principles of different CA125 assays of the present description. In a conventional CA125 immunoassay (FIG. 1A), both the capturing agent and the tracer are monoclonal antibodies, which detect different protein epitopes of CA125. In an antibody-lectin sandwich assay (FIG. 1B), a CA125 protein epitope-specific antibody is used as the capturing agent, while a glycan-specific $Eu^{3+}$-labelled lectin is used as the tracer. In an antibody-lectin nanoparticle sandwich assay (FIG. 1C), a CA125 protein epitope-specific antibody is used as the capturing agent, while a glycan-specific $Eu^{3+}$-doped nanoparticle-labelled lectin is used as the tracer.

A combination of biotinylated Ov197 mAb (as a capture antibody for CA125 on streptavidin plates) and Eu$^{3+}$-labelled Ov185 mAb (as a tracer antibody) were used in a DELFIA® time resolved fluorescence (TRF) immunoassay. The mAbs used detect different protein epitopes on CA125. The basic principle of this conventional CA125 immunoassay is illustrated in FIG. 1A, while experimental details are given in Example 1.

First, three different CA125-containing samples, namely OVCAR-3-derived purified CA125, amniotic fluid (AF), and placental homogenate (Pla) were assayed as set forth above.

Figure 2:
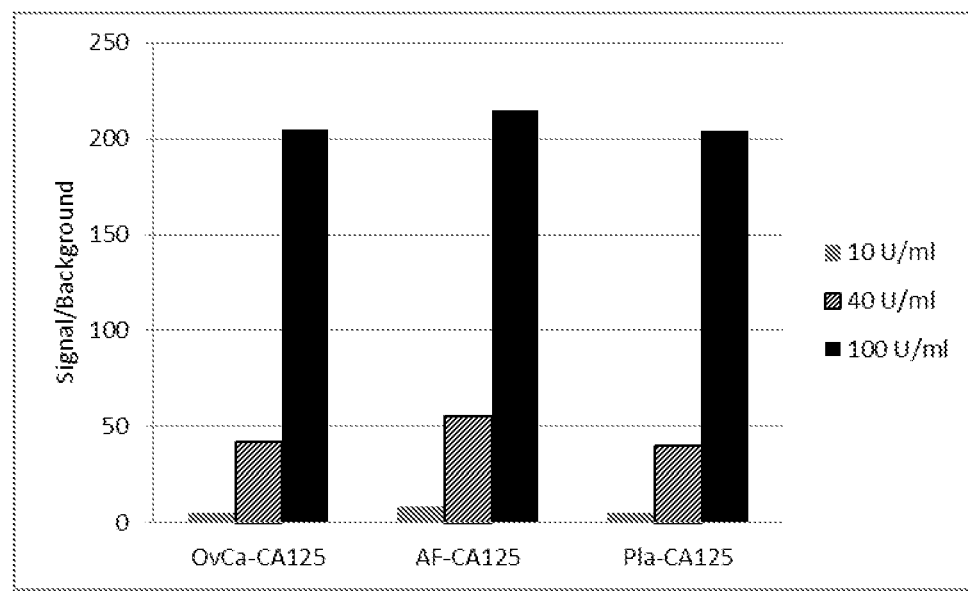
FIG. 2 shows the results of a conventional CA125 Immunoassay. CA125 from primary ovarian carcinoma cell line OVCAR-3 (OvCa-CA125), amniotic fluid (AF-CA125) and placental homogenate (Pla-CA125) were captured on biotinylated Ov197 mAb. $Eu^{3+}$ chelates-labelled Ov185 mAb was used as a tracer. All origins of CA125 showed almost similar signals/background ratios indicating that equal amounts of CA125 were used regardless of the origin.

The results showed that CA125 of different origins gave almost similar net signals indicating that the amount of CA125 protein in each sample was almost the same (FIG. 2). Thus, the conventional CA125 immunoassay cannot be used for discriminating malignant CA125 from normal CA125.

Figure 3:
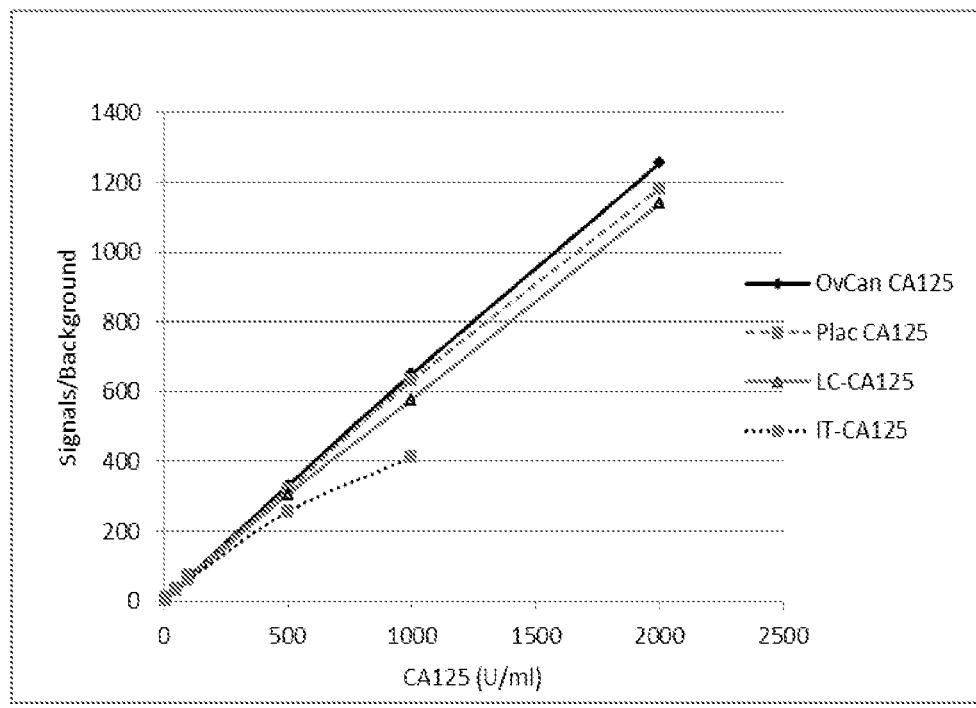
FIG. 3 illustrates the conventional CA125 immunoassay with four different CA125-containing samples, namely purified CA125 from a primary ovarian carcinoma cell line OVCAR-3 (OvCa-CA125), placental homogenate (Pla-CA125), ascites fluid of liver cirrhosis (LC-CA125) and immature teratoma (IT-CA125). Different amounts of CA125 ranging from 5 to 2000 U/ml (with the exception of IT-CA125 whose amount ranged from 5 to 1000 U/ml) were captured on bioOv197 mAb and traced by Ov185-$Eu^{3+}$ mAb used as tracer. Different samples could not be discriminated from each other. Only IT-CA125 showed deflection at higher concentration (500 to 1000 U/ml) due to matrix effect as the concentration of CA125 in ascites fluid of IT was only 904 U/ml.

Next, the above results were verified in a larger dynamic range with another set of origins of CA125. To this end, CA125 of four different origins, i.e. cancerous CA125 from OVCAR-3 cell line and normal/benign CA125 from placental homogenate (Pla) and two ascites of liver cirrhosis (LC) and immature teratoma (IT), were applied on the Ov197 plates in an amount ranging from 5 to 2000 U/ml with the exception of IT-CA125 which was used in an amount ranging from 5 to 1000 U/ml. Ov185 was used as a tracer for detecting the binding of CA125 of different origins to Ov197. These results confirmed that the conventional CA125 immunoassay cannot be used for discriminating CA125 of different origins from each other (FIG. 3).

Example 3: Anti-CA125 Antibody-Lectin Sandwich Assay

In these experiments, CA125 of three different origins were used in amounts ranging from 10 to 100 U/ml in TSA-BSA 1%. CA125 was captured on the biotinylated Ov185 anti-CA125 antibody. A panel of Eu$^{3+}$-labelled plant as well as human lectins were used as tracers as shown schematically in FIG. 1B and described in detail in Example 1. Most reactions showed high backgrounds in relation to the predominantly low specific signals.

Figure 4:
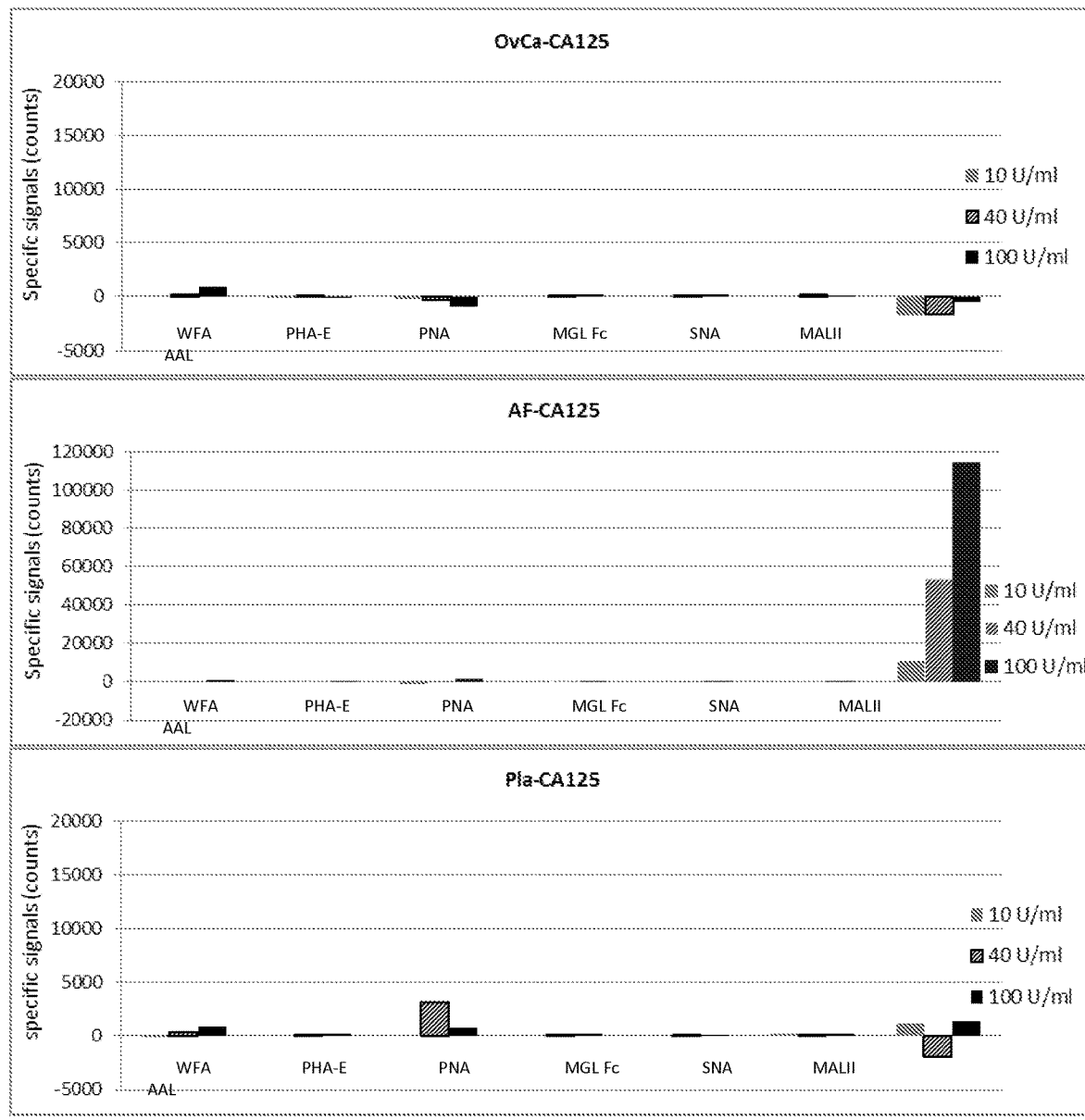
FIG. 4 demonstrates that, with the exception of AAL, no discrimination between three different origins of CA125 was achieved when lectins labelled with Europium N1 chelates were used as tracers. OVCAR-3 cell line was used as a source for cancerous CA125 (OvCa-CA125), whereas amniotic fluid and placental homogenate were used as sources for normal CA125 (AF-CA125 and Pla-CA125, respectively). AAL was able to discriminate amniotic fluid-derived CA125 from cancerous and placental CA125. Note the high levels of background signals set forth in Table 3 for each of the lectins in relation to the predominantly low specific signals (Signal-background) shown on the y-axis.

FIG. 4 shows that none of the lectins employed was able to discriminate between non-malignant CA125 and EOC-derived CA125. The lowest background was obtained with MGL but the net signals from the reactions with CA125 were very poor. Background signals for each of the lectins employed are shown in Table 3 below.

TABLE 3

| Lectin Eu-chelates | Background signals (counts) |
| --- | --- |
| WFA | 2066 |
| PHA E | 1918 |
| PNA | 50479 |
| MGL | 248 |
| SNA | 844 |
| MALII | 5624 |
| AAL | 11747 |

Figure 5:
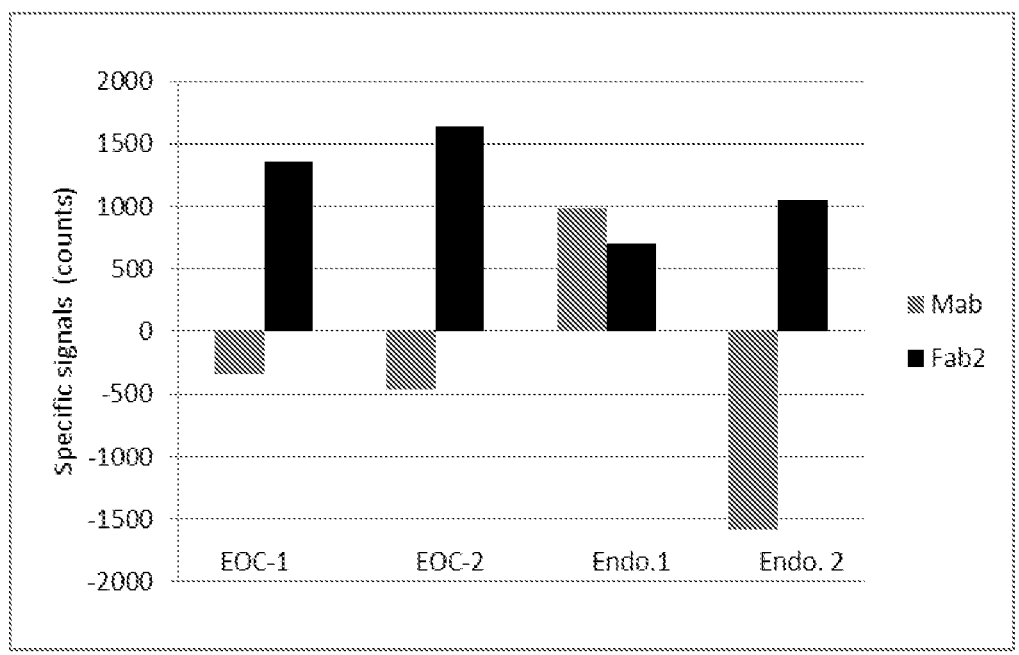
FIG. 5 shows the results of anti-CA125 antibody-AAL lectin assay with four clinical samples. CA125 from two EOC and two endometriosis serum samples (EOC-1, EOC-2, Endo.1, and Endo.2, respectively) were captured on bioOv197 mAb as well as on Fab2 fraction thereof, and $Eu^{3+}$ chelates-labelled AAL lectin used as a tracer. No remarkable discrimination between EOC and endometriosis patient samples was achieved.

On the other hand, AAL (lectin from mushroom *Aleuria amantia*) was able to react with amniotic fluid-derived CA125 but not with cancerous or placental CA125. In order to test whether or not AAL could be used for identifying benign CA125 in patients with endometriosis, four clinical serum samples, two from patients with EOC and two from patients with endometriosis, were employed. As shown in FIG. 5, AAL cannot be used for discriminating EOC-derived CA125 from endometriosis-derived CA125. Fab fractions of the capturing antibodies were used in an attempt to reduce the background signals but no significant improvement was achieved.

Example 4: Anti-CA125 Antibody-Lectin Nanoparticle Sandwich Assay

Since the direct Eu-chelate labelling of lectins gave no discrimination between different origins of CA125, lectins were immobilized onto $Eu^{3+}$-doped nanoparticles as described in Example 1 in order to improve functional affinity (avidity effect). Two features of the nanoparticles, in particular, were noticed to contribute to the improvement of the results: 1) signal amplification provided by 30,000 chelates in a 107 nm particle, and 2) the strengthening of the functional affinity of the lectins to their target epitopes through the avidity effect provided by the high density of immobilized lectins on the particle.

In these experiments, four different sources of CA125 were used, namely purified OVCAR-3 derived CA125 (150900 U/ml), placental homogenate (Pla), ascites fluid of liver cirrhosis (LC), and ascites fluid of immature teratoma (IT). Next, 5 to 100 U/ml of CA125 from all four different sources spiked in TSA-BSA were assayed using an antibody-lectin nanoparticle sandwich assay. Biotinylated Ov185 mAb was used as a capturing antibody, while Eu chelate doped nanoparticles loaded with several different plant lectins, namely WGA, WFA, SNA, PHAE, SBA, AAL, UEA, MAA, RCA, PSA, VVL, TJA or PNA, or human C-type lectin receptors (CLR), namely MGL and DC-SIGN, were used as tracers.

Figure 6:
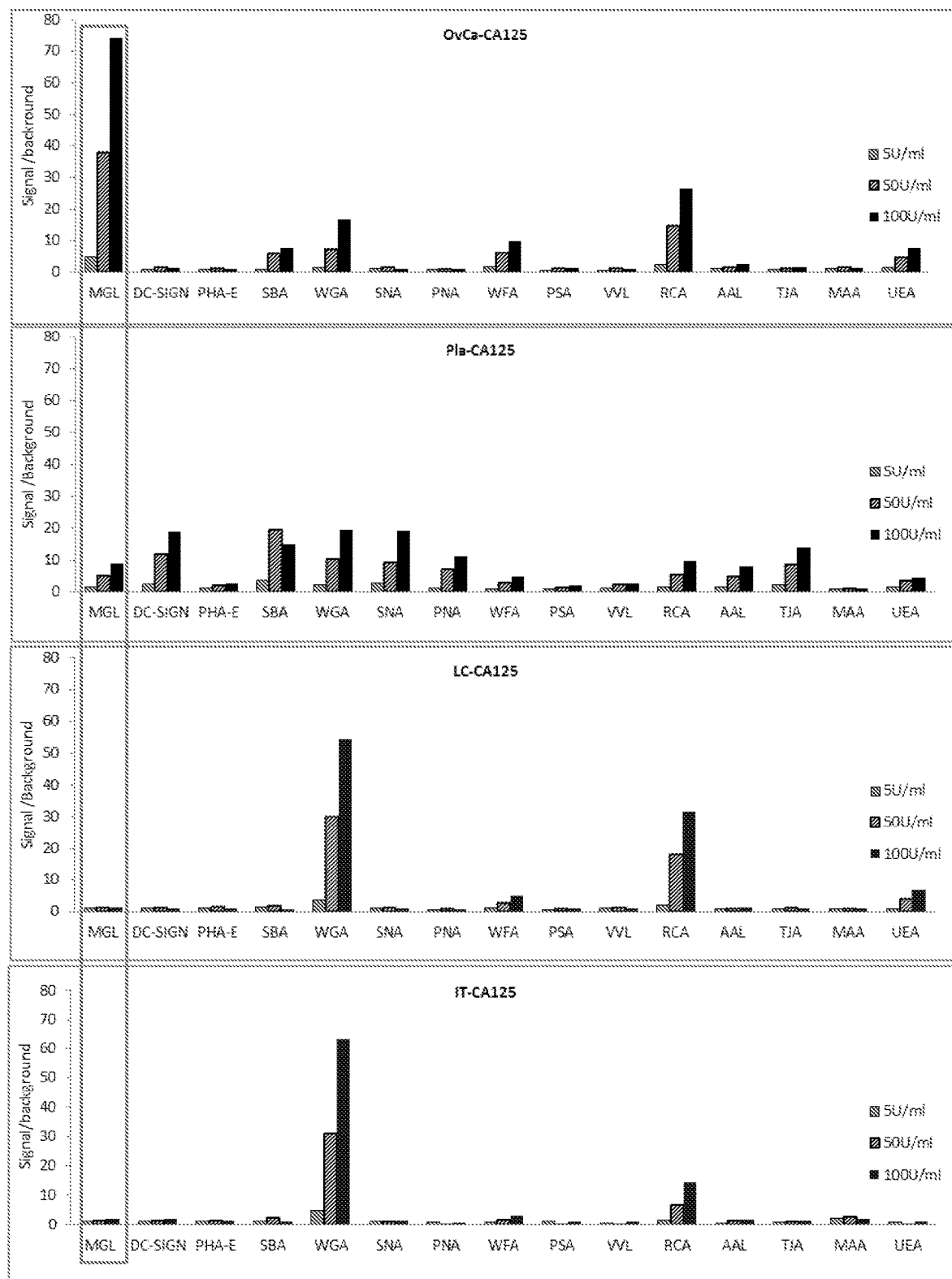
FIG. 6 shows the results of anti-CA125 antibody-lectin nanoparticle assay. CA125 from four different origins in amounts of either 5, 50, or 100 U/ml in TSA-BSA buffer were captured on bio-Ov185 MAb. A panel of plant and human lectins immobilized on $Eu^{3+}$-nanoparticles were used as tracers. Only MGL-NP clearly discriminated OvCa-derived CA125 from CA125 of other origins. Background signals for each of the lectins are shown in Table 4.

As shown in FIG. 6, only human lectin MGL nanoparticles showed enhanced specificity for the EOC-derived CA125. The net signal with EOC-derived CA125 was 10- to 12-fold higher than with placental homogenate-derived CA125 (Pla-CA125). Negligible net signal was obtained with liver cirrhosis-derived CA125 (LC-CA125) and with immature teratoma-derived CA125 (IT-CA125). Background signals for each of the lectins employed are shown in Table 4 below.

TABLE 4

| Lectin coated on Eu-NP | Background signals (counts) |
| --- | --- |
| MGL | 217 |
| DC-SIGN | 416 |
| PHA-E | 30044 |
| SBA | 128 |
| WGA | 4230 |
| SNA | 758 |
| PNA | 959 |
| WFA | 4369 |
| PSA | 1642 |
| VVL | 6659 |
| RCA | 359 |
| TJA | 834 |
| MAA | 3796 |

WGA showed four times more net signals with LC-125 and IT-CA125 than with EOC-derived or placental CA125, while SNA, PHA-E, PNA, VVL and DC-SIGN showed reactivity with only placental CA125 (FIG. 6). The results indicate that none of these lectins are suitable for discriminating EOC-related CA125 from normal or benign CA125.

Figure 7:
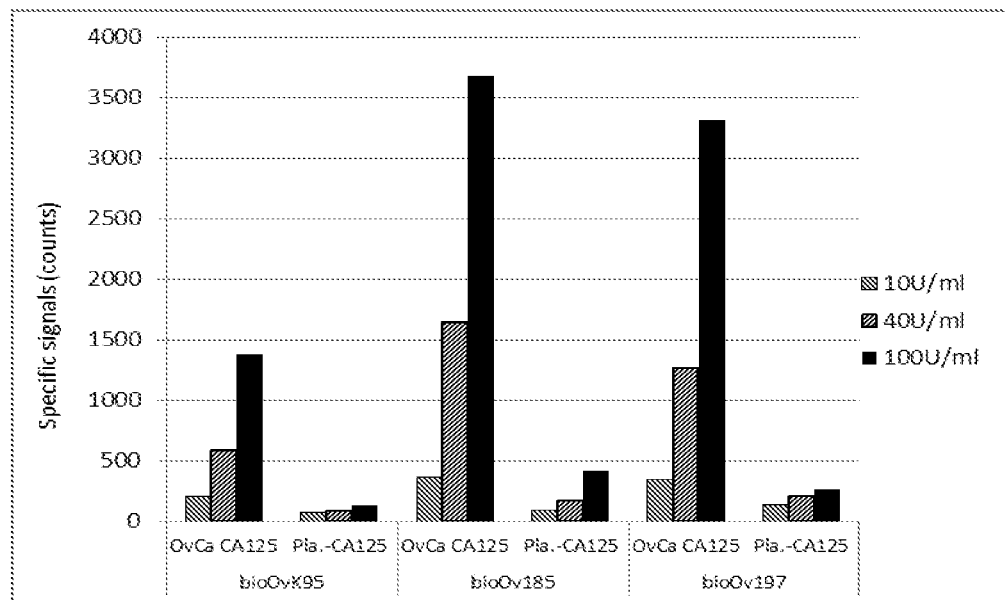
FIG. 7 shows the results of anti-CA125 antibody-MGL nanoparticle assay with different biotinylated capture antibodies (Ovk95, Ov185 and Ov197). $Eu^{3+}$-labelled MGL-NP was used as a tracer. In each case, OvCa-CA125 was discriminated almost 10-fold from Pla-CA125. The highest specific signals were obtained when bioOv185 was used as the capturing antibody.

Next, all three anti-CA125 mAbs (Ov185, Ov197 and OvK95) were compared as capturing agents for CA125 in the MGL nanoparticle assay. Ov185 gave the highest net signals as well as signal/background (S/B) ratio with a very good discrimination between OvCa-derived and normal/benign CA125 antigen. The analytical detection limit was estimated to be less than <5 U/ml for OvCa-derived CA125 (FIG. 7).

Figure 8:
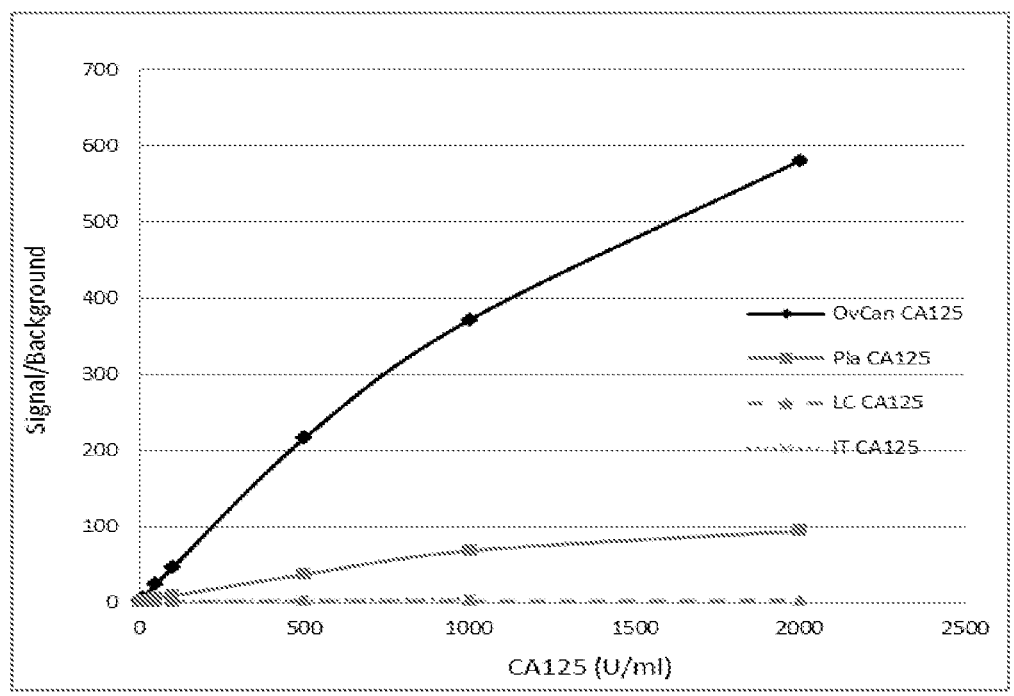
FIG. 8 shows the results of the MGL-NP assay in wider dynamic ranges with four different origins of CA125. CA125 from primary OvCa cell line OVCAR-3 (OvCa-125), placental homogenate (Pla-CA125), and ascites of liver cirrhosis (LC-CA125) and immature teratoma (IT-CA125) were used in an amount of 5 to 2000 U/ml (with the exception of IT-CA125 with concentrations ranging from 5 to 1000 U/ml). No hook effect was observed with concentrations of CA125 even up to 2000 U/ml.

No hook effect was observed even very high concentrations of CA125 were used in the MGL-NP assay (FIG. 8). This is an important result indicating that no false negative results are to be obtained with present method due to very high concentrations of CA125 in a sample to be analysed.

Figure 9:
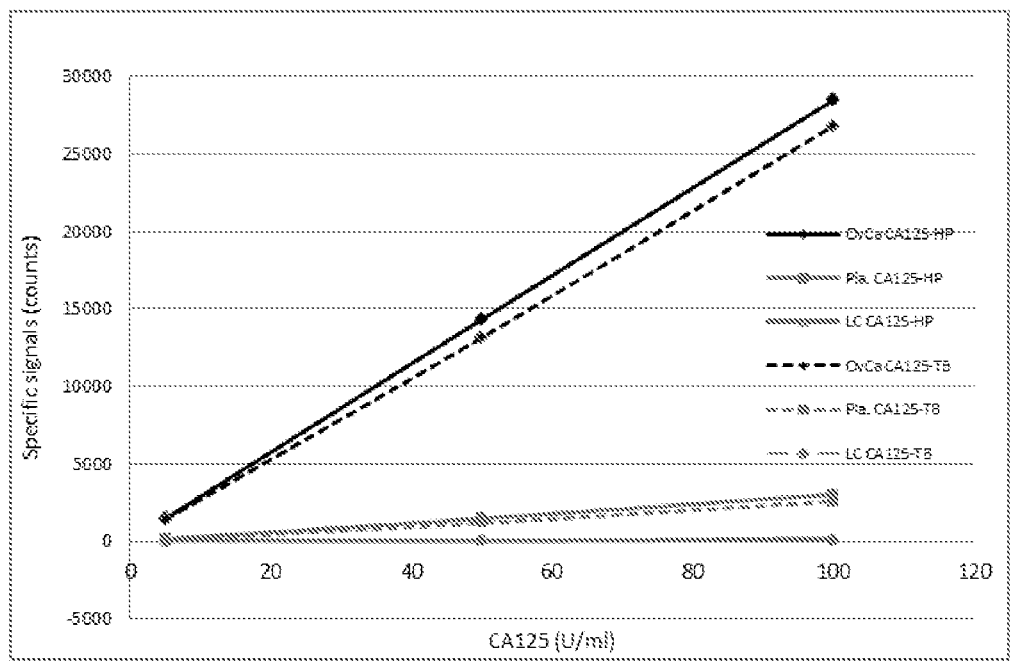
FIG. 9 shows the results of the MGL-NP assay with CA125 samples spiked in healthy pooled male plasma (HP) or in TSA-BSA 1% buffer (TB). Specific signals were almost similar with simple matrices like TSA-BSA 1% and using healthy pooled male plasma.

Example 5: Suitability of Blood Samples for Anti-CA125 Antibody-Lectin Nanoparticle Sandwich Assay After the good separation of OvCa-derived CA125 from CA125 of other origins with the present MGL-Fc NP-assay in simple matrices/buffer (TSA-BSA 1%), the recovery value of the same in complex matrices like human serum/plasma was determined. For this purpose, 5 to 100 U/ml of CA125 from different origins were spiked in parallel in either healthy male pooled plasma or in simple buffer (TSA-BSA 1%) and captured on biotinylated Ov185 mAb on streptavidin microtiter plates and, after washing, finally traced with MGL-Fc NPs to see the recovery rate. Excellent recovery of almost 95 to 110% was achieved indicating that the inherent plasma components do not interfere with the present MGL-Fc nanoparticle assay (FIG. 9).

Example 6: Analyses of Clinical Samples

Figure 10:
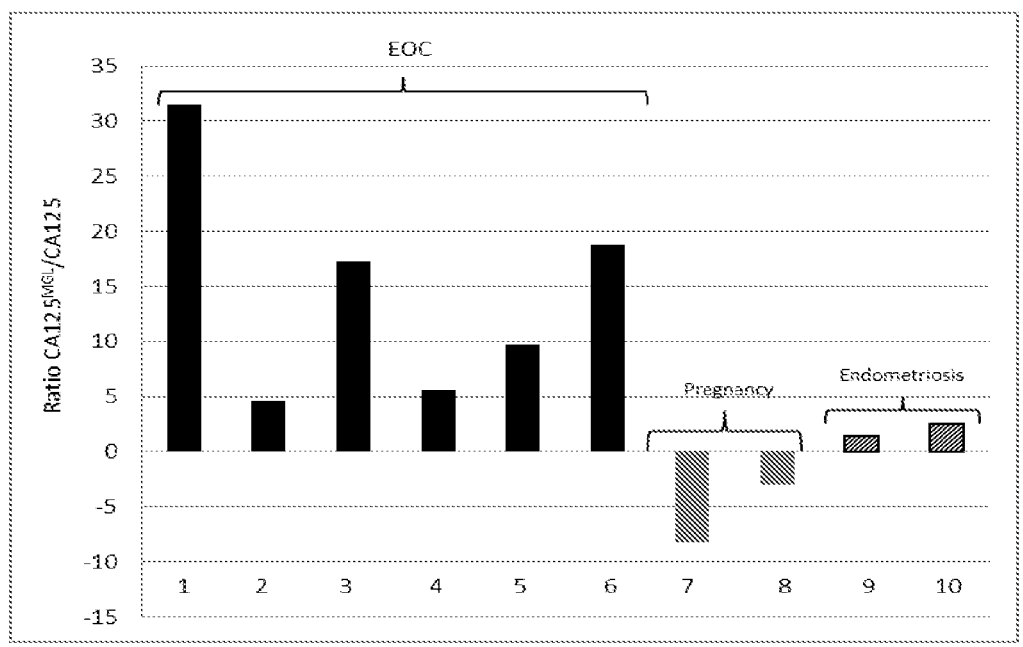
FIG. 10 shows the ratios of specific signals obtained with the present MGL-NP assay and the conventional CA125 immunoassay. EOC serum samples (1-6) showed elevated signals as compared with serum samples of pregnant women (7-8) and two pools of endometriosis samples (9-10). Thus, the MGL-NP assay is able to distinguish EOC-related CA125 from normal or benign CA125.

In order to test whether or not the results obtained with OVACAR-3 cell line-based CA125 antigen could be translated into clinical context, a small cohort of clinical samples was analysed side by side with the present MGL-NP assay and the conventional CA125 immunoassay. The cohort included serum samples of patients with EOC (n=12) and healthy pregnant women (n=2) as wells as pooled serum samples of patients with endometriosis (n=2). Signal ratios obtained with the two methods clearly indicated that clinical EOC samples can indeed be distinguished from clinical endometriosis samples (FIG. 10).

In order to validate the results in a larger cohort and to compare the diagnostic power of CA125$^{MGL}$ to conventional CA125 protein marker and HE4, a number of archived clinical serum samples (n=401) were employed. Serum concentrations of HE4, CA125 protein, and CA125$^{MGL}$ were assessed in 213 sequential samples of 68 ovarian cancer patients were compared with results obtained in 121 patients with endometriosis, 16 patients with endometrial cancer and 51 healthy women as controls (Table 1). All EOC cases were from advanced stages of the disease but 43 serum samples from 32 individual EOC cases belonged to a progression/relapse stage of the disease. These progression/relapse serum samples (n=43) were considered as mimics of the early stages of the disease and, therefore, were treated as a separate group of the clinical samples in some of the analyses performed.

Box Plot Analyses

Figure 11A:
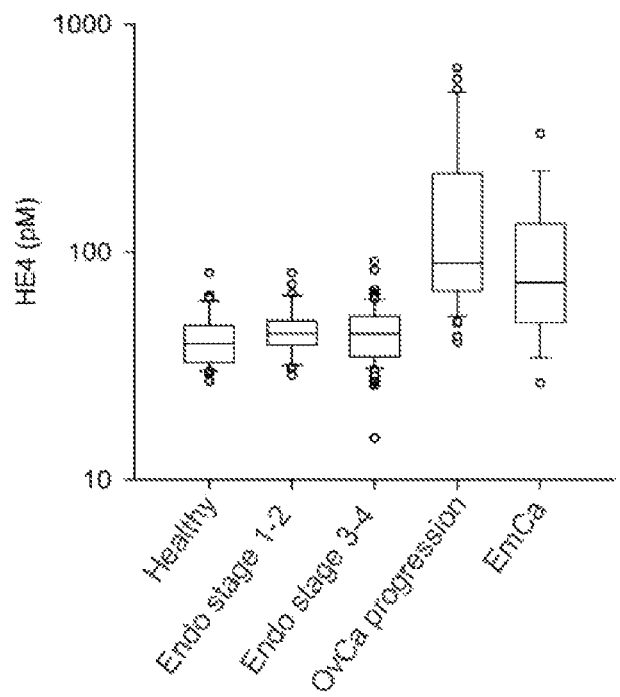
FIG. 11A shows a Box Plot presentation of a conventional HE4 immunoassay with five different groups of clinical serum samples (healthy women as controls n=51, endometriosis stages 1-2 n=33, endometriosis stages 3-4 n=88, EOC progression/relapse cases n=43 (OvCa progression) and endometrial cancer n=16 (EmCa)). Median of each group is shown within the boxes.
Figure 11B:
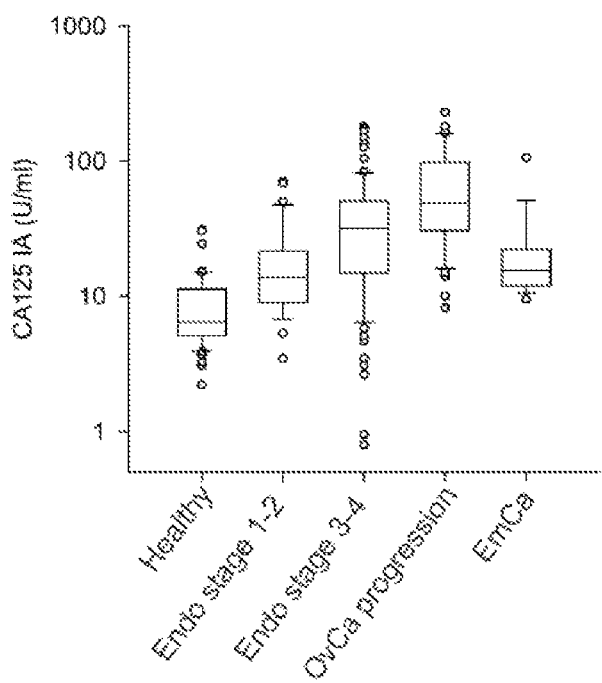
FIG. 11B shows a Box Plot presentation of a conventional CA125 immunoassay with five different groups of clinical serum samples (healthy women as controls n=51, endometriosis stages 1-2 n=33, endometriosis stages 3-4 n=88, EOC progression/relapse cases n=43 (OvCa progression) and endometrial cancer n=16 (EmCa)). Median of each group is shown within the boxes.
Figure 11C:
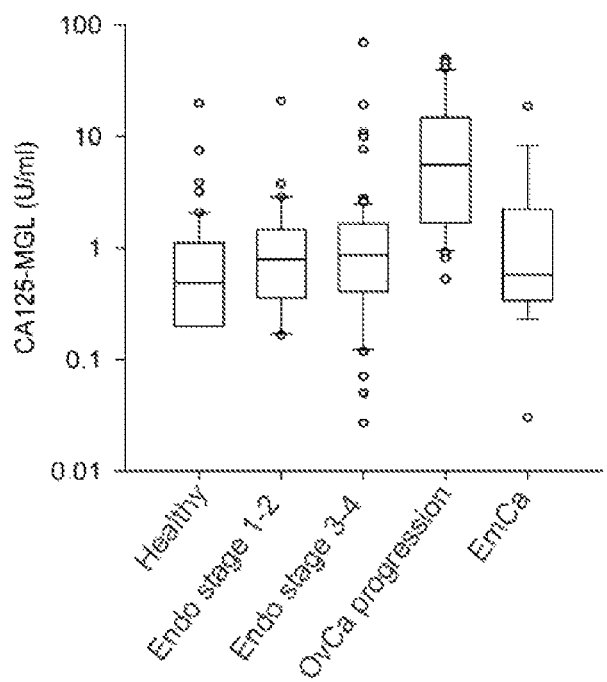
FIG. 11C shows a Box Plot presentation of the MGL-NP assay with five different groups of clinical serum samples (healthy women as controls n=51, endometriosis stage 1-2 n=33, endometriosis stage 3-4 n=88, EOC progression/relapse cases n=43 (OvCa progression), and endometrial cancer n=16 (EmCa)). Median of EOC is 6 while medians of all other groups are only 1.

Box Plot analyses of five different groups of clinical samples (healthy control n=51, endometriosis stages 1-2 n=33, endometriosis stages 3-4 n=88, EOC progression/relapse cases n=43 and endometrial cancer n=16) with respect to their HE4 protein content, CA125 protein content (conventional) and CA125$^{MGL}$ glycoform content are shown in FIGS. 11A to 11C. According to the results, HE4 content was elevated in the EOC group and, to a lesser extent, also in the group of endometrial cancers. The conventional CA125 protein content was elevated in the EOC progression/relapse group as compared with the groups of healthy controls and endometrial cancers, but the CA125 protein content was overlapping with the group of endometriosis stages 3-4. CA125$^{MGL}$ content, in turn, was elevated only in the EOC progression/relapse group as compared with all the other groups. Together these results indicate that of the markers studied only CA125$^{MGL}$ can be successfully used for distinguishing clinical EOC cases from the other case groups.

In another series of Box Plot analyses, the CA125$^{MGL}$ assay was applied to the analysis of serum samples from the healthy individuals (n=51), and the endometriosis (n=121) and high-grade serous EOC patients (n=21) and compared them with the conventional CA125 immunoassay values. The median preoperative CA125 values in serum samples of healthy controls, endometriosis patients and EOC patients were 6.4, 24.9 and 700 U/ml, respectively (FIG. 12A), showing significantly elevated concentrations both in endometriosis and EOC as compared with healthy controls. In contrast, median preoperative CA125$^{MGL}$ values (FIG. 12B) did not significantly differ between healthy controls (0.486 U/ml) and endometriosis patients (0.841 U/ml; p=0.073). In EOC group the median CA125$^{MGL}$ was 37.93 U/ml being 45-times higher than in endometriosis. Further, serum samples from endometriosis (n=44) and EOC (n=38) patients with marginally elevated CA125 values (35-200 U/ml) were studied to evaluate the discrimination between malignant and benign conditions by conventional CA125 immunoassay and CA125$^{MGL}$ assay (FIGS. 12C and 12D). As evidenced by FIG. 12D, the CA125$^{MGL}$ assay provided significantly higher (6.1 fold, p-value <0.001) levels in the EOC serum samples as compared with those measured in the endometriosis patients. On the other hand, the difference between healthy controls and endometriosis patients was reduced significantly. A 8.3-fold (p<0.001) difference was observed with the conventional assay, while a 2.5-fold difference still reaching significance (p=0.005) was observed with the CA125$^{MGL}$ assay.

ROC Curve and AUC Analyses

ROC curve analyses for discriminating endometriosis (n=121) from either all sequential EOC cases (n=213), progression/relapse EOC cases (n=43), or advance pre-operative EOC cases (n=29) were performed with respect to HE4, CA125, and CA125$^{MGL}$ either alone or in combination. The ROC curves are shown in FIGS. 13A to 13C, while the obtained AUC values are summarized below.

TABLE 5

AUC values obtained from ROC analysis performed for discriminating endometriosis (n = 121) from all sequential EOC cases (n = 213)

| Marker | AUC |
|---|---|
| HE4 | 0.876 |
| CA125 | 0.776 |
| CA125$^{MGL}$ | 0.815 |
| Combination of all three markers | 0.899 |

TABLE 6

AUC values obtained from ROC analysis performed for discriminating endometriosis (n = 121) from progression/relapse EOC cases (n = 43)

| Marker | AUC |
|---|---|
| HE4 | 0.928 |
| CA125 | 0.759 |
| CA125$^{MGL}$ | 0.870 |
| Combination of all three markers | 0.947 |

TABLE 7

AUC values obtained from ROC analysis performed for discriminating endometriosis (n = 121) from pre-operative EOC cases (n = 29)

| Marker | AUC |
|---|---|
| HE4 | 0.941 |
| CA125 | 0.959 |
| CA125$^{MGL}$ | 0.889 |
| Combination of all three markers | 0.967 |

In the first two analyses, the AUC value for HE4 was higher than for CA125 or CA125$^{MGL}$ because of the negligible false positivity in endometriosis with HE4 (FP=2.5%). Corresponding FP values for CA125 and CA125$^{MGL}$ in endometriosis are 37.2% and 7.4%, respectively.

In the last analysis, which concerned pre-operative serum samples, i.e. samples representing advanced stages of EOC, the AUC value for CA125 was the highest. This result is in accordance with the known diagnostic value of CA125 particularly in advanced EOC.

In each AUC analysis, the AUC value obtained with a combination of all three markers was higher than that of any individual marker.

Assessment of Success Rates

Success rates for markers HE4, CA125, and CA125$^{MGL}$ either alone or in paired combinations were determined regarding the disease group of progression/relapse cases (n=32, the first sequential sample from each individual progression/relapse patient). Each serum sample was classified either as negative or positive for each marker using the following cut-off values: 35 IU/ml for CA125, 70 pM for HE4, and 2 IU/ml for CA125$^{MGL}$.

TABLE SERIES 8

Distribution of serum samples (n = 32) on the basis of their marker positivity or negativity

| | | HE4 + | HE4 − | | | CA125 + | CA125 − | | | HE4 + | HE4 − |
|---|---|---|---|---|---|---|---|---|---|---|---|
| CA125 | + | 13 | 7 | CA125$^{MGL}$ | + | 17 | 6 | CA125$^{MGL}$ | + | 14 | 9 |
| | − | 8 | 4 | | − | 3 | 6 | | − | 7 | 2 |

| | No. positive (%) | No. positive (%) | No. positive (%) |
|---|---|---|---|
| HE4 | 21 (65.6) | — | 21 (65.6) |
| CA125 | 20 (62.5) | 20 (62.5) | — |
| CA125$^{MGL}$ | — | 23 (71.9) | 23 (71.9) |
| Combination | 28 (87.5) | 26 (81.2) | 30 (93.7) |

These results indicate that the success rate of CA125$^{MGL}$ for identifying early EOC cases as afflicted individuals may be improved from 71.9% to 81.2% and further to 93.7% when used in combination with CA125 and HE4, respectively.

Longitudinal Analyses

Relative concentration changes (concentration/cut-off) of HE4, CA125, and CA125$^{MGL}$ in sequential serum samples from EOC cases under progression of the disease (n=29) were determined. All patients were treated for disseminated disease with surgery and chemotherapy and were under surveillance for disease progression. All patients had a significant initial treatment response as judged by both reduction of CA125 values and radiologic response criteria but experienced a verified disease progression during follow-up. Samples with low positive levels were included, but high preoperative/early treatment phases were excluded from the analysis. Cut-off values used HE4, CA125, and CA125$^{MGL}$ were 70 pM, 35 U/ml, and 2 U/ml, respectively.

The results showed that in 69% of the cases (20/29) the level of CA125$^{MGL}$ was increased stronger than the other two markers upon progression of the disease. Furthermore, CA125$^{MGL}$ displayed earlier increase than HE4 and CA125 in 31% of the cases (9/29). Thus, clinicians could be alarmed much earlier of a possible relapse if CA125$^{MGL}$ was used to monitor patients under treatment for EOC. The median concentration of CA125$^{MGL}$ in samples obtained at or just before EOC progression was 7.97 U/ml. Some examples of the longitudinal analyses performed are shown in FIG. 14.

Example 7: Effect of Hormonal Status on Serum Levels of CA125$^{MGL}$

Serum samples of healthy premenopausal women and women with endometriosis analysed earlier for CA125 and HE4 (Hallamaa et al., Gynecol. Oncol., 2012, 125:667-672) were now assayed for CA125$^{MGL}$ by the present MGL-NP assay. Results show that both CA125$^{MGL}$ and HE4 assays can be carried out at any phase of the menstrual cycle and irrespective of hormonal medication without distortion of the results (FIGS. 15A and 15C, respectively). This finding extends the applicability of these two markers in clinical practice. On the other hand, the conventional CA125 assay showed significant differences between different stages of the menstrual cycle (FIG. 15B).

The invention claimed is:

1. A method of determining a gynaecological disease state in a subject, said method comprising:
   (a) obtaining a sample from said subject,
   (b) assaying said sample for the level of CA125 which binds to macrophage galactose-type lectin (CA125$^{MGL}$), comprising: contacting the sample with a nanoparticle-immobilized MGL (MGL-NP) to form a CA125$^{MGL}$-NP complex,
   (c) measuring the level of the CA125$^{MGL}$-NP complex to obtain the level of CA125$^{MGL}$ in the sample,
   (d) comparing the measured level of CA125$^{MGL}$ in said sample with that of a control sample or a predetermined threshold value, wherein the control sample or the predetermined threshold value is from healthy subjects or subjects known to have or at risk for having endometriosis; and
   (e) determining epithelial ovarian cancer (EOC) in said subject when increased level of CA125$^{MGL}$ is measured as compared to the CA125$^{MGL}$ in the control sample or the predetermined threshold value.

2. The method according to claim 1, wherein non-increased level of CA125$^{MGL}$ in said sample as compared with that of the control sample or the predetermined threshold value indicates that said subject does not have or is not at risk of having EOC.

3. The method according to claim 1, wherein the method further comprises assaying a sample obtained from said subject for CA125 protein concentration, and comparing the detected CA125 protein concentration with that of the control sample or the predetermined threshold value.

4. The method according to claim 3, wherein increased CA125 protein concentration in combination with increased level of CA125$^{MGL}$ further indicates that said subject has or is at risk of having EOC.

5. The method according to claim 1, further comprising determining the concentration of CA125 protein, wherein increased CA125 protein concentration in combination with non-increased level of CA125$^{MGL}$ indicates that said subject has or is at risk of having endometriosis.

6. The method according to claim 1, wherein the method further comprises assaying a sample obtained from said subject for the HE4 protein concentration, and comparing the detected HE4 protein concentration with that of the control sample or the predetermined threshold value.

7. The method according to claim 6, wherein increased HE4 protein concentration in combination with increased level of CA125$^{MGL}$ further indicates that said subject has or is at risk of having EOC.

8. The method according to claim 1 for diagnosing, prognosing, or monitoring a gynaecological disease, wherein said gynaecological disease is EOC.

9. The method according to claim 8, wherein said monitoring is for monitoring onset of said gynaecological disease, for monitoring any change in risk of having or developing said gynaecological disease, for monitoring response to treatment, for monitoring relapse of said gynaecological disease, or for monitoring recurrence of said gynaecological disease.

10. The method according to claim 8, wherein the assaying step (b) is repeated at least twice at different time points.

11. The method according to claim 10, wherein said time points are selected, independently from each other, from the group consisting of time points before diagnosis, time points after diagnosis, time points before treatment of said gynaecological disease, time points during treatment of said gynaecological disease, and time points after treatment of said gynaecological disease.

12. The method according to claim 11, wherein said treatment of said gynaecological disease is selected from the group consisting of surgery, radiation therapy, and chemotherapy.

13. The method according to claim 8, wherein the monitoring is carried out during or after treatment of EOC, and wherein said subject is determined as having relapse or recurrence of EOC or as being at risk of relapse or recurrence of EOC, if the level of $CA125^{MGL}$ is higher than in the control sample or above the predetermined threshold value.

14. The method according to claim 1, wherein assaying the level of CA125 binding to said MGL-NP of step (b) comprises contacting said sample with an anti-CA125 antibody to capture CA125 contained in the sample prior to contacting with MGL-NP of step (b), wherein the measuring step (c) comprises measuring the level of $CA125^{MGL}$ which binds to both $CA125^{MGL}$-NP and the-anti-CA125 antibody and wherein the MGL-NP is labeled.

15. The method according to claim 1, wherein assaying the level of CA125 binding to said MGL-NP of step (b) further comprises contacting the $CA125^{MGL}$-NP complex with an anti-CA125antibody prior to the measuring step c, wherein the measuring step (c) comprises measuring the level of CA125 which binds to both the nanoparticle-immobilized MGL ($CA125M^{GL}$), and the-anti-CA125 antibody, and wherein the anti-CA125 antibody is labeled.

16. The method according to claim 1, wherein said sample is selected from the group consisting of urine, blood, serum, plasma, peritoneal cavity fluid, and tissue samples.

17. The method according to claim 1, wherein all the dimensions of said nanoparticle are less than about 1000 nm, about 500 nm or less, about 100 nm or less, or about 50 nm or less.

18. The method according to claim 17, wherein said nanoparticle is selected from the group consisting of protein nanoparticles, mineral nanoparticles, glass nanoparticles, nanoparticle crystals, metal nanoparticles, plastic nanoparticles, polystyrene nanoparticles, poly(ethylene glycol) nanoparticles, polyethylene nanoparticles, poly(acrylic acid) nanoparticles, poly(methyl methacrylate) nanoparticles, polysaccharide nanoparticles, colloidal gold nanoparticles, silver nanoparticles, quantum dots, carbon nanoparticles, porous silica nanoparticles, and liposomes.

19. The method according to claim 17, wherein said nanoparticle is doped with a lanthanide chelate.

20. The method according to claim 17, wherein said nanoparticle is doped with the lanthanide chelate, europium (III).

* * * * *